(12) United States Patent
Omar et al.

(10) Patent No.: US 11,857,372 B2
(45) Date of Patent: Jan. 2, 2024

(54) SYSTEM AND METHOD FOR GRAPHICAL USER INTERFACE WITH FILTER FOR ULTRASOUND IMAGE PRESETS

(71) Applicant: BFLY OPERATIONS, INC., Burlington, MA (US)

(72) Inventors: Murad Omar, New Haven, CT (US); Karl Thiele, St. Petersburg, FL (US); Abraham Neben, Guilford, CT (US); Elizabeth Lauer, Campbell, CA (US); Gianfranco Bocchio, Brooklyn, NY (US)

(73) Assignee: BFLY OPERATIONS, INC., Burlington, MA (US)

( * ) Notice: Subject to any disclaimer, the term of this patent is extended or adjusted under 35 U.S.C. 154(b) by 0 days.

(21) Appl. No.: 17/986,252

(22) Filed: Nov. 14, 2022

(65) Prior Publication Data
US 2023/0148994 A1 May 18, 2023

Related U.S. Application Data

(60) Provisional application No. 63/279,040, filed on Nov. 12, 2021.

(51) Int. Cl.
*G06F 3/04847* (2022.01)
*A61B 8/00* (2006.01)
(Continued)

(52) U.S. Cl.
CPC .......... *A61B 8/469* (2013.01); *A61B 8/0866* (2013.01); *A61B 8/0891* (2013.01);
(Continued)

(58) Field of Classification Search
CPC ..... A61B 8/469; A61B 8/0866; A61B 8/0891; A61B 8/4483; A61B 8/465; A61B 8/54;
(Continued)

(56) References Cited

U.S. PATENT DOCUMENTS

| 5,315,999 | A | 5/1994 | Kinicki et al. |
| 6,468,212 | B1 * | 10/2002 | Scott ..................... A61B 8/463 600/440 |

(Continued)

FOREIGN PATENT DOCUMENTS

| KR | 102227873 B1 | 3/2021 |
| WO | 2019099652 A1 | 5/2019 |

OTHER PUBLICATIONS

International Search Report and Written Opinion of the International Searching Authority issued in corresponding application PCT/US2022/049792 dated Feb. 24, 2023 (17 pages).

(Continued)

*Primary Examiner* — Hien L Duong
(74) *Attorney, Agent, or Firm* — Carter, DeLuca & Farrell LLP

(57) ABSTRACT

A graphical user interface displayed by a processing device in operative communication with an ultrasound device may include a preset filter option that provides an easy way to switch between different presets which belong to a preset family. The user uses the preset filter feature to cycle through the different presets in the family while remaining on the same screen that is showing ultrasound images collected in real time. The imaging depth remains the same while the user is using the preset filter feature to select the preset within a family. Other settings such as time-gain compensation may not remain the same when cycling between presets. The preset filter feature allows a user to continuously view and assess the ultrasound images being collected in real time while cycling through the presets in the family.

19 Claims, 19 Drawing Sheets

(51) Int. Cl.
  *A61B 8/08* (2006.01)
  *G06F 3/0482* (2013.01)
(52) U.S. Cl.
  CPC ............ *A61B 8/4483* (2013.01); *A61B 8/465* (2013.01); *A61B 8/54* (2013.01); *A61B 8/56* (2013.01); *A61B 8/585* (2013.01); *G06F 3/0482* (2013.01); *G06F 3/04847* (2013.01)
(58) Field of Classification Search
  CPC ......... A61B 8/56; A61B 8/585; G06F 3/0482; G06F 3/04847
  See application file for complete search history.

(56) References Cited

U.S. PATENT DOCUMENTS

| | | | |
|---|---|---|---|
| 9,408,587 B2* | 8/2016 | Pelissier | A61B 8/467 |
| 9,898,242 B2 | 2/2018 | Rust et al. | |
| 10,387,713 B2 | 8/2019 | Yang et al. | |
| 10,402,074 B2 | 9/2019 | Jin et al. | |
| 10,517,573 B2 | 12/2019 | Yang et al. | |
| 10,617,391 B2 | 4/2020 | Yang et al. | |
| 11,020,090 B2 | 6/2021 | Yoon et al. | |
| 2002/0087061 A1 | 7/2002 | Lifshitz et al. | |
| 2006/0241455 A1 | 10/2006 | Shvarts | |
| 2008/0208045 A1 | 8/2008 | Rielly | |
| 2008/0269610 A1 | 10/2008 | Burla et al. | |
| 2014/0088428 A1* | 3/2014 | Yang | G06F 3/04847 600/443 |
| 2016/0139789 A1* | 5/2016 | Jin | G06T 3/60 715/771 |
| 2016/0157822 A1 | 6/2016 | Jin et al. | |
| 2016/0228091 A1* | 8/2016 | Chiang | A61B 8/462 |
| 2016/0345936 A1* | 12/2016 | Cho | G01S 7/52084 |
| 2017/0124700 A1* | 5/2017 | Sarojam | A61B 8/523 |
| 2018/0085043 A1* | 3/2018 | Panicker | A61B 5/204 |
| 2018/0220995 A1* | 8/2018 | Pelissier | A61B 8/5207 |
| 2019/0038260 A1 | 2/2019 | Lee et al. | |
| 2019/0043387 A1* | 2/2019 | Dickie | A61B 8/467 |
| 2019/0247025 A1* | 8/2019 | Jin | A61B 8/565 |
| 2019/0307428 A1* | 10/2019 | Silberman | A61B 8/467 |
| 2019/0365350 A1 | 12/2019 | Chiang | |
| 2021/0015456 A1 | 1/2021 | Chiang et al. | |
| 2021/0052254 A1* | 2/2021 | Holmes | A61B 8/488 |
| 2021/0096243 A1* | 4/2021 | Gafner | A61B 8/462 |
| 2021/0353260 A1 | 11/2021 | Srinivasa Naidu et al. | |
| 2022/0125416 A1* | 4/2022 | Lee | G16H 40/63 |

OTHER PUBLICATIONS

Brian Starkoff, "Ultrasound physical principles in today's technology", AJUM, vol. 17, No. 1, pp. 4-10 (2014).

* cited by examiner

SYSTEM AND METHOD FOR GRAPHICAL USER INTERFACE WITH FILTER FOR ULTRASOUND IMAGE PRESETS

CROSS-REFERENCE TO RELATED APPLICATION

The present application claims the benefit of and priority to U.S. Provisional Application No. 63/279,040, filed on Nov. 12, 2021. The entire contents of the foregoing application are incorporated by reference herein.

FIELD

Generally, the aspects of the technology described herein relate to ultrasound data collection. Some aspects relate to configuring an ultrasound system with imaging parameter values.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using a probe), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

Recent advances in ultrasound technology have enabled large arrays of ultrasound transducers and ultrasound circuitry to be integrated onto a semiconductor chip or one or more semiconductor chips packaged together (e.g., in a stacked configuration) to form an ultrasound-on-chip. An ultrasound-on-chip may form the core of an ultrasound device, which may be in the form, for example, of a handheld ultrasound probe, a wearable ultrasound patch, or an ingestible ultrasound pill. When the ultrasound transducers are capacitive micromachined ultrasonic transducers (CMUTs), the transducers may provide sufficient range in frequency to enable use of the ultrasound device for whole-body scanning. Furthermore, when the ultrasound device is in operative communication with a processing device such as a smartphone, tablet, or laptop via a specific software application, the system is cheaper and more portable than conventional ultrasound systems.

The present disclosure provides for graphical user interfaces (GUIs) to control ultrasound imaging using such an ultrasound system. Due to the low cost and portability of such an ultrasound system, unlike conventional ultrasound systems that are designed for use by sonographers experienced in ultrasound imaging, the present system may be used by users who are less experienced in ultrasound imaging. In particular, the ultrasound system of the present disclosure provides simple and intuitive controls that allow a user to configure the ultrasound system with one of many available presets. A preset may include multiple (e.g., tens or hundreds or thousands of) ultrasound imaging parameter values used by the ultrasound device and/or the processing device in their ultrasound imaging operation. Each given preset may be optimized for imaging a particular type of anatomy and/or for imaging in a particular clinical application. Thus, a less-experienced user can simply choose a preset rather than manually select the appropriate parameters.

When the ultrasound system is capable of whole-body scanning, the number of presets available may be large. It may be challenging to incorporate so many options into an easy-to-use GUI for mobile processing devices, which generally have a smaller display screen than a conventional ultrasound system. Thus, the present disclosure provides for a novel GUI configured to facilitate selection of presets within a smaller display area while displaying ultrasound images in real-time.

Some related presets may be organized in preset families. A GUI displayed by the processing device may include a preset filter option that provides an easy way to switch between different presets which belong to a preset family. The user uses the preset filter feature to cycle through the different presets in the family while remaining on the same screen that is showing ultrasound images collected in real time. The imaging depth also remains the same while the user is using the preset filter to select the preset within a family. When using the preset filter to cycle through presets within a preset family, the user does not need to leave the screen that is showing ultrasound images in real time to return to a preset menu to change to a different preset within the same family. Thus, the preset filter GUI also allows a user to try different presets in a family to find the appropriate preset, with fewer clicks or taps required since the clinician does not need to go back to a preset menu. The user may be able to continuously view and assess the ultrasound images being collected in real time while cycling through the presets in the family. The preset filter GUI offers improved workflow for finding the appropriate preset for any view, patient, clinician, etc., since different patients provide different imaging challenges and different clinicians have different imaging preferences.

According to one aspect of the above embodiment, a smartphone or tablet in operative communication with an ultrasound device is disclosed. The smartphone is configured to receive from a user a selection of a first preset from a preset menu displayed by the smartphone or tablet. The preset menu includes a plurality of user-selectable presets. The smartphone is configured to control ultrasound imaging operation based on the first preset, where controlling the ultrasound imaging operation includes controlling ultrasound imaging operation of the ultrasound device and ultrasound imaging operation of the smartphone or tablet, and use a default imaging depth associated with the first preset and a default time-gain compensation (TGC) setting associated with the first preset in the ultrasound imaging operation. The smartphone is also configured to receive from the user a selection of a first imaging depth different from the default imaging depth and a first TGC setting different from the default TGC setting associated with the first preset and to use the first imaging depth and the first TGC setting in the ultrasound imaging operation. The smartphone is further configured to receive from the user an activation of a preset filter option displayed by the smartphone or tablet, thereby selecting a second preset within a same preset family as the first preset and to control the ultrasound imaging operation based on the second preset and use the first imaging depth and a default TGC setting associated with the second preset and different from the first TGC setting in the ultrasound imaging operation. The smartphone is also configured to receive from the user a selection of second TGC setting different from the default TGC setting associated with the second preset and different from the first TGC setting and to use the first imaging depth and the second TGC setting in the ultrasound imaging operation. The smartphone is further configured to receive from the user an activation of the preset filter option, thereby selecting the first preset and to control the ultrasound imaging operation based on the first preset and use the first imaging depth and the first TGC setting in the ultrasound imaging operation.

Implementations of the above embodiment may include one or more of the following features. According to one aspect of the above embodiment, the first preset and the second preset each may include a different set of ultrasound imaging parameter values that control transmit, analog processing, digital pre-processing and beamforming, coherent post-processing, and incoherent post-processing. The preset family may include a plurality of presets optimized for imaging a same anatomy, a same anatomical region, and/or a same type of anatomy. The first preset may include a standard preset and the second preset may include a deep preset. The first preset may include a harmonics preset and the second preset may include a fundamentals preset. The preset family may include two or more of an abdomen preset, an abdomen deep preset, and an aorta and gallbladder preset. The preset family may include two or more of a musculoskeletal (MSK) preset, an MSK soft tissue preset, and a small organ preset. The preset family may include two or more of an obstetric first month and gynecological preset, and an obstetric second and third months preset. The first preset may include a vascular access preset and the second preset may include a carotid preset. The preset family may include two or more of a lung artifacts preset, a lung consolidation preset, and a lung tissue preset. Repeated activation of the preset filter option may cycle through presets within the preset family. A number of presets in the preset family is smaller than a number of the plurality of user-selectable presets in the preset menu. A subset of the plurality of user-selectable presets in the preset menu may not be in preset families. The smartphone or tablet may be configured to not display the preset filter option if a user selects a preset in the subset. The smartphone or tablet may be configured to not display a subset of available presets in the preset menu. The smartphone or tablet may be configured to display the first preset and the second preset in the preset menu. The ultrasound device may include an ultrasound-on-chip. The smartphone or tablet may be configured, when controlling the ultrasound imaging operation of the ultrasound device, to transmit commands to the ultrasound device to configure the ultrasound device with parameter values of the first preset. The smartphone or tablet may be configured to save the first TGC setting prior to or upon receiving from the user the activation of the preset filter thereby selecting the second preset.

According to another aspect of the above embodiment, a smartphone or tablet in operative communication with an ultrasound device is disclosed. The smartphone is configured to receive from a user a selection of a first preset from a preset menu displayed by the smartphone or tablet, where the preset menu includes a plurality of user-selectable presets and to control ultrasound imaging operation based on the first preset, where controlling the ultrasound imaging operation includes controlling ultrasound imaging operation of the ultrasound device and ultrasound imaging operation of the smartphone or tablet. The smartphone is also configured to receive from the user an activation of a preset filter option displayed by the smartphone or tablet, thereby selecting a second preset within a same preset family as the first preset and to control the ultrasound imaging operation based on the second preset.

BRIEF DESCRIPTION OF THE DRAWINGS

Embodiments of the present disclosure are described herein with reference to the accompanying drawings, wherein.

DETAILED DESCRIPTION

Figure 1:
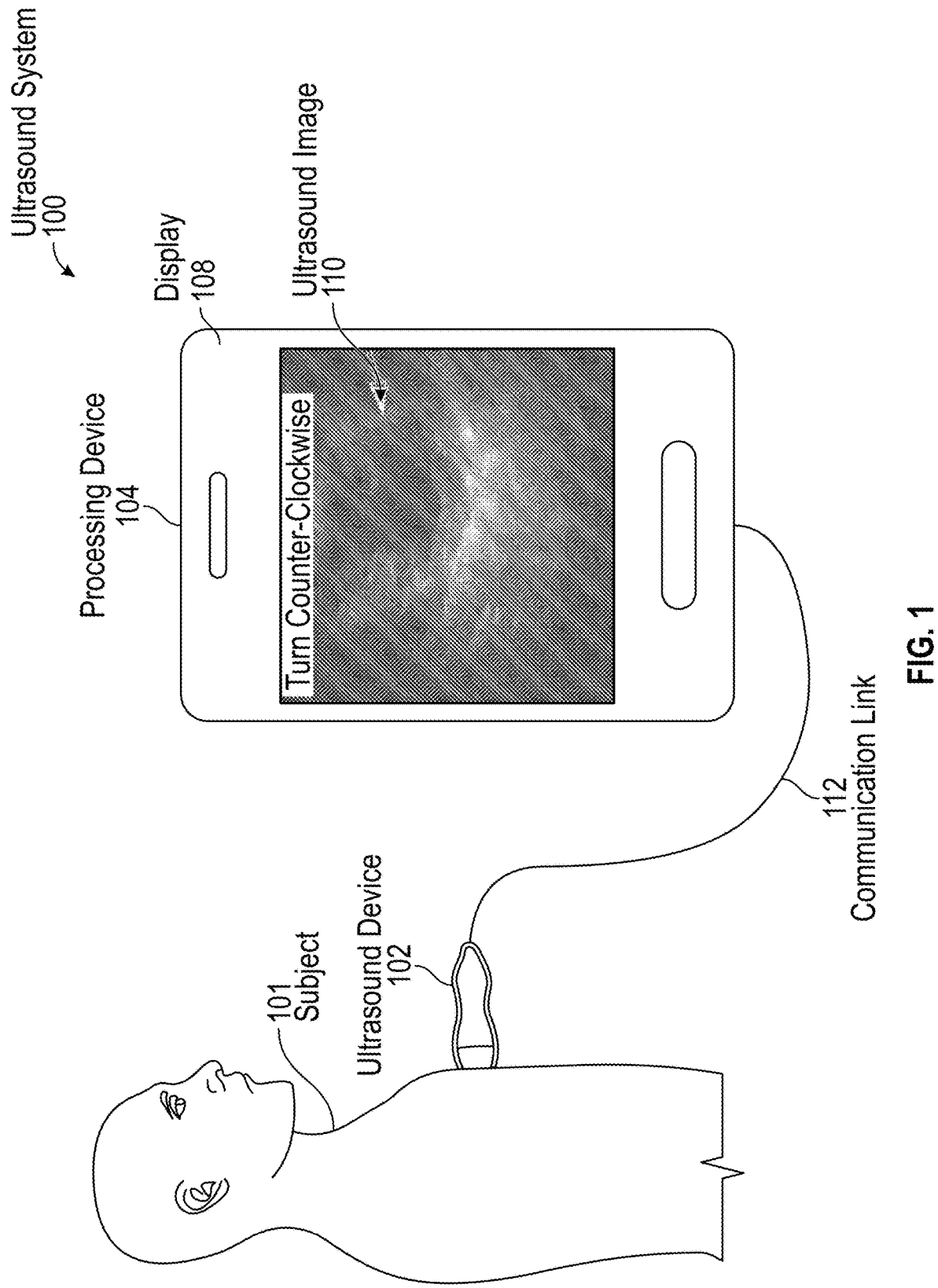
FIG. 1 is a schematic diagram of an ultrasound system according to one embodiment of the present disclosure.

Embodiments of the present disclosure are described in detail with reference to the drawings, in which like reference numerals designate identical or corresponding elements in each of the several views.

FIG. 1 shows an exemplary ultrasound system 100 including an ultrasound device 102 configured to obtain an ultrasound image of a target anatomical view of a subject 101. As shown, the ultrasound system 100 includes an ultrasound device 102 that is communicatively coupled to the processing device 104 by a communication link 112. The processing device 104 may be configured to receive ultrasound data from the ultrasound device 102 and use the received ultrasound data to generate an ultrasound image 110 on a display (which may be touch-sensitive) of the processing device 104.

Figure 2:
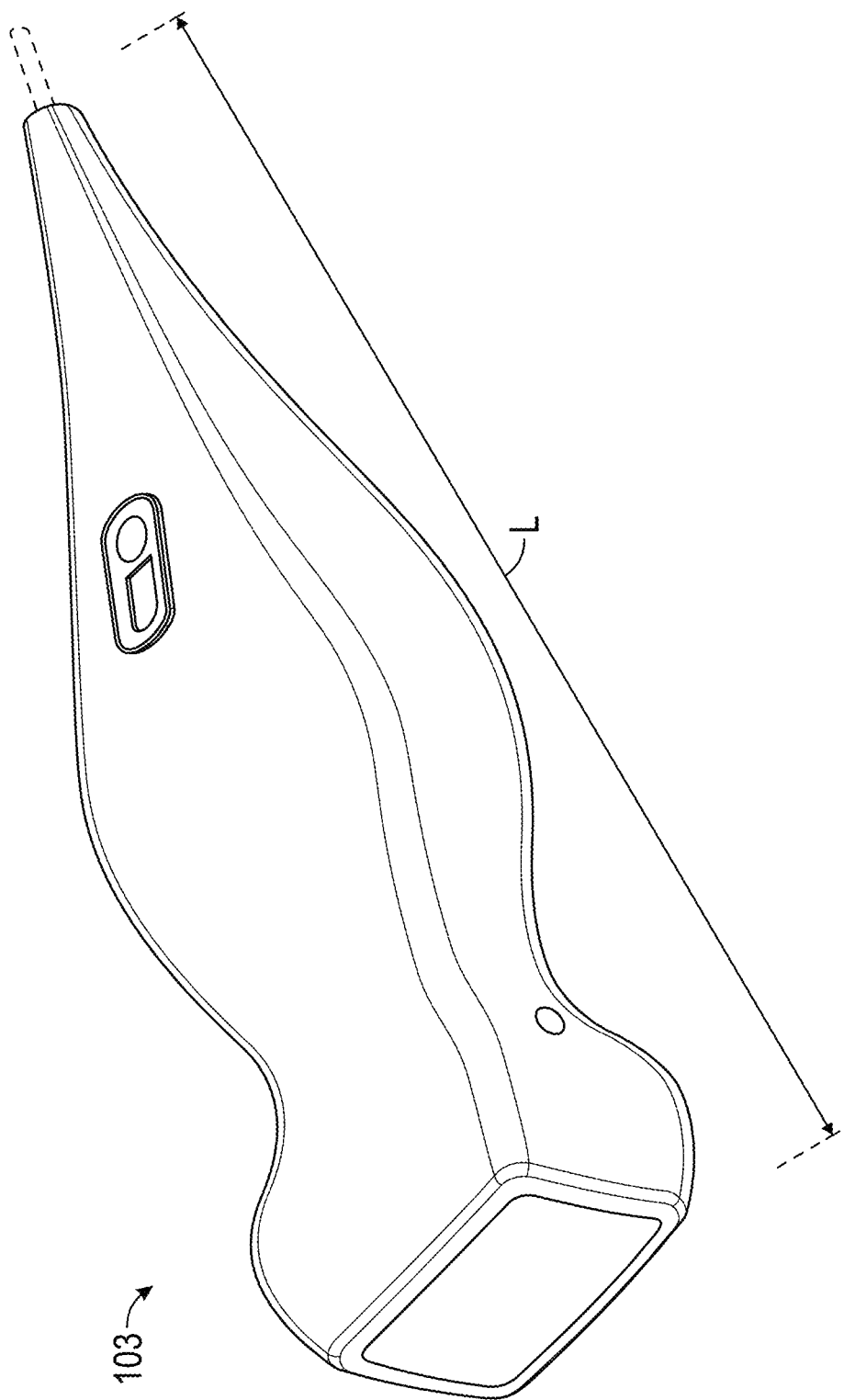
FIG. 2 is a perspective view of an ultrasound probe according to one embodiment of the present disclosure.

The ultrasound device 102 may be configured to generate ultrasound data. The ultrasound device 102 may be configured to generate ultrasound data by, for example, emitting acoustic waves into the subject 101 and detecting the reflected acoustic waves. The detected reflected acoustic wave may be analyzed to identify various properties of the tissues through which the acoustic wave traveled, such as a density of the tissue. The ultrasound device 102 may be implemented in any of a variety of ways. For example, the ultrasound device 102 may be implemented as a handheld device (as shown in FIGS. 1 and 2) or as a patch that is coupled to patient using, for example, an adhesive or a strap. The patch may be configured to wirelessly transmit data collected by the patch to one or more external devices for further processing. In other embodiments, the single ultrasound probe may be embodied in a pill that may be swallowed by a patient. The pill may be configured to transmit, wirelessly, data collected by the ultrasound probe within the pill to one or more external devices for further processing.

The ultrasound device 102 may transmit ultrasound data to the processing device 104 using the communication link 112. The communication link 112 may be a wired or wireless communication link. In some embodiments, the communication link 112 may be implemented as a cable such as a Universal Serial Bus (USB) cable or a Lightning cable. In these embodiments, the cable may also be used to transfer power from the processing device 104 to the ultrasound device 102. In other embodiments, the communication link 112 may be a wireless communication link such as a BLUETOOTH, WiFi, or ZIGBEE wireless communication link.

Figure 4:
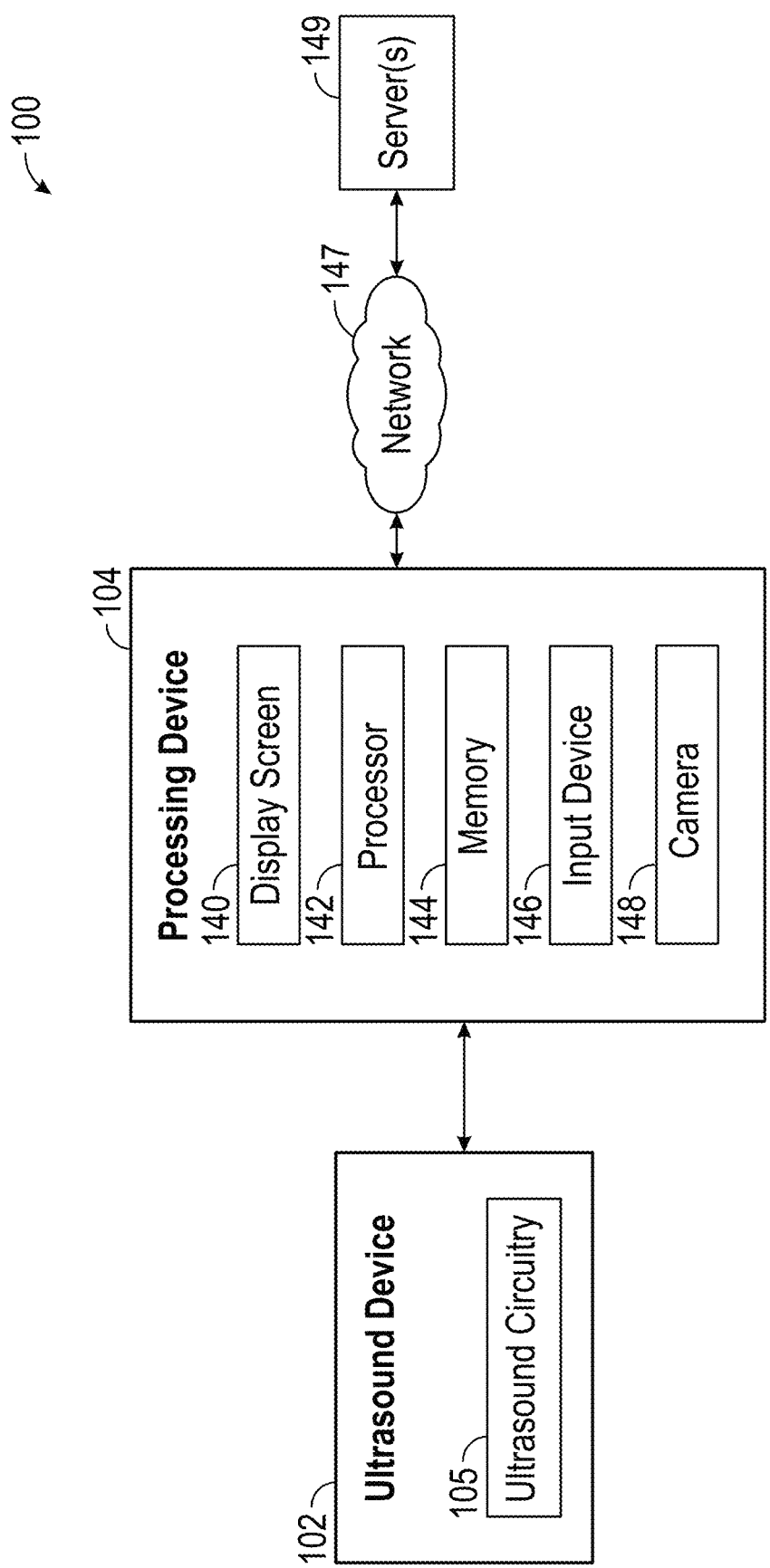
FIG. 4 is a schematic block diagram of the ultrasound system of FIG. 1 according to one embodiment of the present disclosure.

The processing device 104 may include one or more processing elements such as a processor 142 of FIG. 4 configured to, for example, process ultrasound data received from the ultrasound device 102. Additionally, the processing device 104 may include one or more storage elements such as memory 144, which may be a non-transitory computer readable medium configured to, for example, store instructions that may be executed by the processor 142 and/or store all or any portion of the ultrasound data received from the ultrasound device 102. It should be appreciated that the processing device 104 may be implemented in any of a variety of ways. For example, the processing device 104 may be implemented as a mobile device (e.g., a mobile smartphone, a tablet, or a laptop, etc.) with an integrated display screen 108 as shown in FIG. 1. In other examples, the processing device 104 may be implemented as a stationary device such as a desktop computer.

FIG. 2 illustrates an exemplary handheld ultrasound probe 103, in accordance with certain embodiments described herein, which may be used as the ultrasound device 102. The handheld ultrasound probe 103 may implement any of the ultrasound devices described herein. The handheld ultrasound probe 103 may have a suitable dimension and weight. For example, the ultrasound probe 103 may have a cable for wired communication with a processing device, and may have a length L about 100 mm-300 mm (e.g., 175 mm) and a weight about 200 grams-500 grams (e.g., 312 g). In another example, the ultrasound probe 103 may be capable of communicating with a processing device wirelessly. As such, the handheld ultrasound probe 103 may have a length about 140 mm and a weight about 265 g. It is appreciated that other dimensions and weight may be possible. Further description of ultrasound devices and systems may be found in U.S. Pat. No. 9,521,991, the content of which is incorporated by reference herein in its entirety; and U.S. Pat. No. 11,311,274, the content of which is incorporated by reference herein in its entirety.

Figure 3:
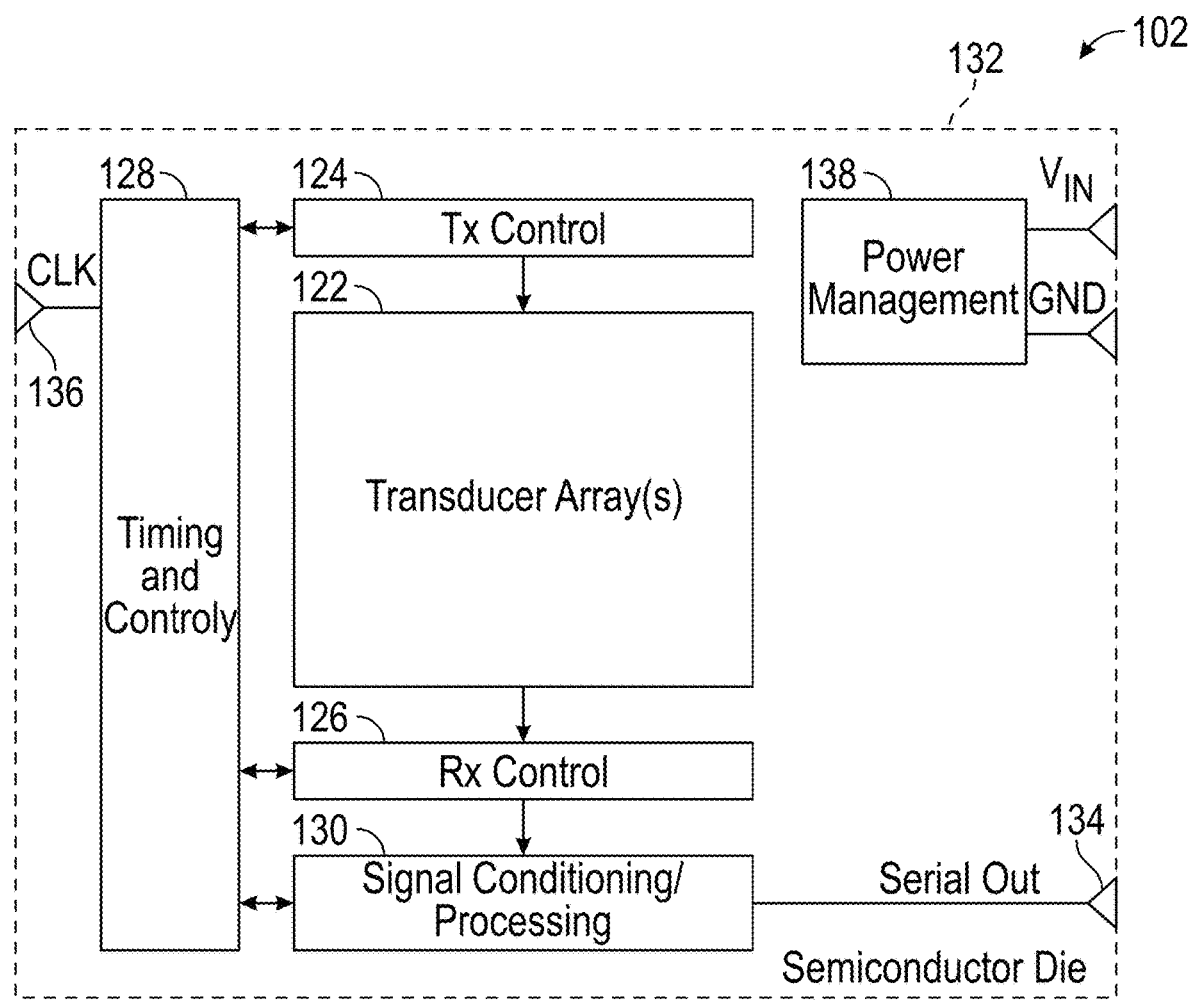
FIG. 3 is a schematic block diagram of an ultrasound device according to one embodiment of the present disclosure.

FIG. 3 is a block diagram of an example of the ultrasound device 102 in accordance with some embodiments of the technology described herein. The illustrated ultrasound device 102 may include one or more ultrasonic transducer arrangements (e.g., arrays) 122, transmit (TX) circuitry 124, receive (RX) circuitry 126, a timing and control circuit 128, a signal conditioning/processing circuit 130, and/or a power management circuit 138.

The one or more ultrasonic transducer arrays 122 may take on any of numerous forms, and aspects of the present technology do not necessarily require the use of any particular type or arrangement of ultrasonic transducer cells or ultrasonic transducer elements. For example, multiple ultrasonic transducer elements in the ultrasonic transducer array 122 may be arranged in one-dimension, or two-dimensions. Although the term "array" is used in this description, it should be appreciated that in some embodiments the ultrasonic transducer elements may be organized in a non-array fashion. In various embodiments, each of the ultrasonic transducer elements in the array 122 may, for example, include one or more capacitive micromachined ultrasonic transducers (CMUTs), or one or more piezoelectric micromachined ultrasonic transducers (PMUTs).

In a non-limiting example, the ultrasonic transducer array 122 may include between approximately 6,000-10,000 (e.g., 8,960) active CMUTs on the chip, forming an array of hundreds of CMUTs by tens of CMUTs (e.g., 140×64). The CMUT element pitch may be between 147-250 um, such as 208 um, and thus, result in the total dimension of between 10-50 mm by 10-50 mm (e.g., 29.12 mm×13.312 mm).

In some embodiments, the TX circuitry 124 may, for example, generate pulses that drive the individual elements of, or one or more groups of elements within, the ultrasonic transducer array(s) 122 so as to generate acoustic signals to be used for imaging. The RX circuitry 126, on the other hand, may receive and process electronic signals generated by the individual elements of the ultrasonic transducer array(s) 122 when acoustic signals impinge upon such elements.

With further reference to FIG. 3, in some embodiments, the timing and control circuit 128 may be, for example, responsible for generating all timing and control signals that are used to synchronize and coordinate the operation of the other components of the ultrasound device 102. In the example shown, the timing and control circuit 128 is driven by a single clock signal CLK supplied to an input port 136. The clock signal CLK may be, for example, a high-frequency clock used to drive one or more of the on-chip circuit components. In some embodiments, the clock signal CLK may, for example, be a 1.5625 GHz or 2.5 GHz clock used to drive a high-speed serial output device (not shown) in the signal conditioning/processing circuit 130, or a 20 Mhz or 40 MHz clock used to drive other digital components on the die 132, and the timing and control circuit 128 may divide or multiply the clock signal CLK, as necessary, to drive other components on the die 132. In other embodiments, two or more clocks of different frequencies (such as those referenced above) may be separately supplied to the timing and control circuit 128 from an off-chip source.

In some embodiments, the output range of a same (or single) transducer unit in an ultrasound device may be anywhere in a range of 1-12 MHz (including the entire frequency range from 1-12 MHz), making it a universal solution, in which there is no need to change the ultrasound heads or units for different operating ranges or to image at different depths within a patient. That is, the transmit and/or receive frequency of the transducers of the ultrasonic transducer array may be selected to be any frequency or range of frequencies within the range of 1 MHz-12 MHz. The ultrasound device 102 described herein may thus be used for a broad range of medical imaging tasks including, but not limited to, imaging a patient's liver, kidney, heart, bladder, thyroid, carotid artery, lower venous extremity, and performing central line placement. Multiple conventional ultrasound probes would have to be used to perform all these imaging tasks. By contrast, a single universal ultrasound device 102 may be used to perform all these tasks by operating, for each task, at a frequency range appropriate for the task, as shown in the examples of Table 1 together with corresponding depths at which the subject may be imaged.

TABLE 1

Illustrative depths and frequencies at which an ultrasound device implemented in accordance with embodiments described herein may image a subject.

| Organ | Frequencies | Depth (up to) |
| --- | --- | --- |
| Liver/Right Kidney | 2-5 MHz | 15-20 cm |
| Cardiac (adult) | 1-5 MHz | 20 cm |
| Bladder | 2-5 MHz; 3-6 MHz | 10-15 cm; 5-10 cm |
| Lower extremity venous | 4-7 MHz | 4-6 cm |
| Thyroid | 7-12 MHz | 4 cm |
| Carotid | 5-10 MHz | 4 cm |
| Central Line Placement | 5-10 MHz | 4 cm |

The power management circuit 138 may be, for example, responsible for converting one or more input voltages VIN from an off-chip source into voltages needed to carry out operation of the chip, and for otherwise managing power consumption within the ultrasound device 102. In some embodiments, for example, a single voltage (e.g., 12V, 80V, 100V, 120V, etc.) may be supplied to the chip and the power management circuit 138 may step that voltage up or down, as necessary, using a charge pump circuit or via some other DC-to-DC voltage conversion mechanism. In other embodiments, multiple different voltages may be supplied separately to the power management circuit 138 for processing and/or distribution to the other on-chip components.

In the embodiment shown above, all of the illustrated elements are formed on a single semiconductor die 132. It should be appreciated, however, that in alternative embodiments one or more of the illustrated elements may be instead located off-chip, in a separate semiconductor die, or in a separate device. Alternatively, one or more of these components may be implemented in a DSP chip, a field programmable gate array (FPGA) in a separate chip, or a separate application specific integrated circuitry (ASIC) chip. Additionally, and/or alternatively, one or more of the components in the beamformer may be implemented in the semiconductor die 132, whereas other components in the beamformer may be implemented in an external processing device in hardware or software, where the external processing device is capable of communicating with the ultrasound device 102.

In addition, although the illustrated example shows both TX circuitry 124 and RX circuitry 126, in alternative embodiments only TX circuitry or only RX circuitry may be employed. For example, such embodiments may be employed in a circumstance where one or more transmission-only devices are used to transmit acoustic signals and one or more reception-only devices are used to receive acoustic signals that have been transmitted through or reflected off of a subject being ultrasonically imaged.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components.

In some embodiments, the ultrasonic transducer elements of the ultrasonic transducer array 122 may be formed on the same chip as the electronics of the TX circuitry 124 and/or RX circuitry 126. The ultrasonic transducer arrays 122, TX circuitry 124, and RX circuitry 126 may be, in some embodiments, integrated in a single ultrasound probe. In some embodiments, the single ultrasound probe may be a hand-held probe including, but not limited to, the hand-held probes described below with reference to FIG. 4.

A CMUT may include, for example, a cavity formed in a CMOS wafer, with a membrane overlying the cavity, and in some embodiments sealing the cavity. Electrodes may be provided to create an ultrasonic transducer cell from the covered cavity structure. The CMOS wafer may include integrated circuitry to which the ultrasonic transducer cell may be connected. The ultrasonic transducer cell and CMOS wafer may be monolithically integrated, thus forming an integrated ultrasonic transducer cell and integrated circuit on a single substrate (the CMOS wafer).

In the example shown, one or more output ports 134 may output a high-speed serial data stream generated by one or more components of the signal conditioning/processing circuit 130. Such data streams may be, for example, generated by one or more USB 3.0 modules, and/or one or more 10 GB, 40 GB, or 100 GB Ethernet modules, integrated on the die 132. It is appreciated that other communication protocols may be used for the output ports 134.

In some embodiments, the signal stream produced on output port 134 can be provided to a computer, tablet, or smartphone for the generation and/or display of two-dimensional, three-dimensional, and/or tomographic images. In some embodiments, the signal provided at the output port 134 may be ultrasound data provided by the one or more beamformer components or auto-correlation approximation circuitry, where the ultrasound data may be used by the computer (external to the ultrasound device) for displaying the ultrasound images. In embodiments in which image formation capabilities are incorporated in the signal conditioning/processing circuit 130, even relatively low-power devices, such as smartphones or tablets which have only a limited amount of processing power and memory available for application execution, can display images using only a serial data stream from the output port 134. As noted above, the use of on-chip analog-to-digital conversion and a high-speed serial data link to offload a digital data stream is one of the features that helps facilitate an "ultrasound on a chip" solution according to some embodiments of the technology described herein.

The ultrasound probe 103 such as that shown in FIG. 2 may be used in various imaging and/or treatment (e.g., HIFU) applications, and the particular examples described herein should not be viewed as limiting. In one illustrative implementation, for example, an imaging device including an N×M planar or substantially planar array of CMUT elements may itself be used to acquire an ultrasound image of a subject (e.g., a person's abdomen) by energizing some or all of the elements in the ultrasonic transducer array(s) 122 (either together or individually) during one or more transmit phases, and receiving and processing signals generated by some or all of the elements in the ultrasonic transducer array(s) 122 during one or more receive phases, such that during each receive phase the CMUT elements sense acoustic signals reflected by the subject. In other implementations, some of the elements in the ultrasonic transducer array(s) 122 may be used only to transmit acoustic signals and other elements in the same ultrasonic transducer array(s) 122 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single ultrasound device 102 or on a single die 132.

FIG. 4 illustrates a schematic block diagram of the ultrasound system 100 which may implement various aspects of the technology described herein. In some embodiments, ultrasound system 100 may include the ultrasound device 102, the processing device 104, a communication network 147, and one or more servers 149. The ultrasound device 102 may be configured to generate ultrasound data that may be employed to generate an ultrasound image. The ultrasound device 102 may be constructed in any of a variety of ways. In some embodiments, the ultrasound device 102 includes a transmitter that transmits a signal to a transmit beamformer which in turn drives transducer elements within a transducer array to emit pulsed ultrasound signals into a structure, such as a patient. The pulsed ultrasound signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. In some embodiments, the ultrasound device 102 may include an ultrasound circuitry 105 (e.g., transducer arrays 122, signal conditioning/processing circuit 130, etc.) that may be configured to generate the ultrasound data. For example, the ultrasound device 102 may include semiconductor die 132 for implementing the various techniques described in.

Reference is now made to the processing device 104. In some embodiments, the processing device 104 may be communicatively coupled to the ultrasound device 102 (wirelessly or in a wired fashion (e.g., by a detachable cord or cable) to implement at least a portion of the process for approximating the auto-correlation of ultrasound signals. For example, one or more beamformer components may be implemented on the processing device 104. In some embodiments, the processing device 104 may include one or more processors 142, which may include specially-programmed and/or special-purpose hardware such as the ASIC chip. The processor 142 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network.

In some embodiments, the processing device 104 may be configured to process the ultrasound data received from the ultrasound device 102 to generate ultrasound images for display on the display screen 140. The processing may be performed by, for example, the processor(s) 142. The processor(s) 142 may also be adapted to control the acquisition of ultrasound data with the ultrasound device 102. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

In some embodiments, the processing device 104 may be configured to perform various ultrasound operations using the processor(s) 142 (e.g., one or more computer hardware processors) and one or more articles of manufacture that include non-transitory computer-readable storage media such as the memory 144. The processor(s) 142 may control writing data to and reading data from the memory 144 in any suitable manner. To perform certain of the processes described herein, the processor(s) 142 may execute one or more processor-executable instructions stored in one or more non-transitory computer-readable storage media (e.g., the memory 144), which may serve as non-transitory computer-readable storage media storing processor-executable instructions for execution by the processor(s) 142.

The camera 148 may be configured to detect light (e.g., visible light) to form an image. The camera 148 may be on the same face of the processing device 104 as the display screen 140. The display screen 140 may be configured to display images and/or videos, and may be, for example, a liquid crystal display (LCD), a plasma display, and/or an organic light emitting diode (OLED) display on the processing device 104. The input device 146 may include one or more devices capable of receiving input from a user and transmitting the input to the processor(s) 142. For example, the input device 146 may include a keyboard, a mouse, a microphone, touch-enabled sensors on the display screen 140, and/or a microphone. The display screen 140, the input device 146, the camera 148, and/or other input/output interfaces (e.g., speaker) may be communicatively coupled to the processor(s) 142 and/or under the control of the processor 142.

It should be appreciated that the processing device 104 may be implemented in any of a variety of ways. For example, the processing device 104 may be implemented as a handheld device such as a mobile smartphone or a tablet. Thereby, a user of the ultrasound device 102 may be able to operate the ultrasound device 102 with one hand and hold the processing device 104 with another hand. In other examples, the processing device 104 may be implemented as a portable device that is not a handheld device, such as a laptop. In yet other examples, the processing device 104 may be implemented as a stationary device such as a desktop computer. The processing device 104 may be connected to the network 147 over a wired connection (e.g., via an Ethernet cable) and/or a wireless connection (e.g., over a WiFi network). The processing device 104 may thereby communicate with (e.g., transmit data to or receive data from) the one or more servers 149 over the network 147. For example, a party may provide from the server 149 to the processing device 104 processor-executable instructions for storing in one or more non-transitory computer-readable storage media (e.g., the memory 144) which, when executed, may cause the processing device 104 to perform ultrasound processes. FIG. 4 should be understood to be non-limiting. For example, the ultrasound system 100 may include fewer or more components than shown and the processing device 104 and ultrasound device 102 may include fewer or more components than shown. In some embodiments, the processing device 104 may be part of the ultrasound device 102.

Figure 15:
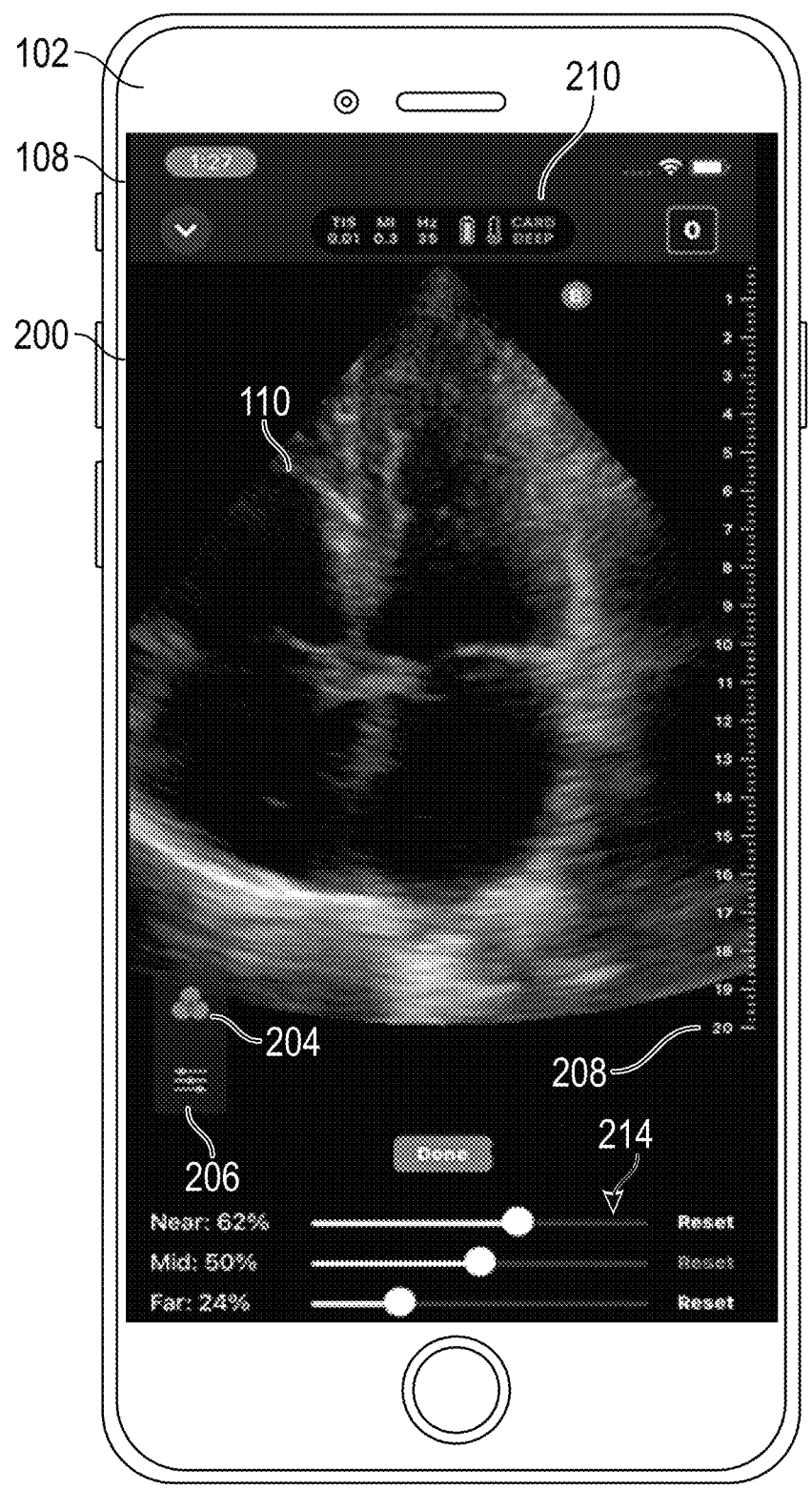
FIG. 15 is a view of the GUI showing adjustment of the TGC settings for the second preset filter according to one embodiment of the present disclosure.
Figure 16:
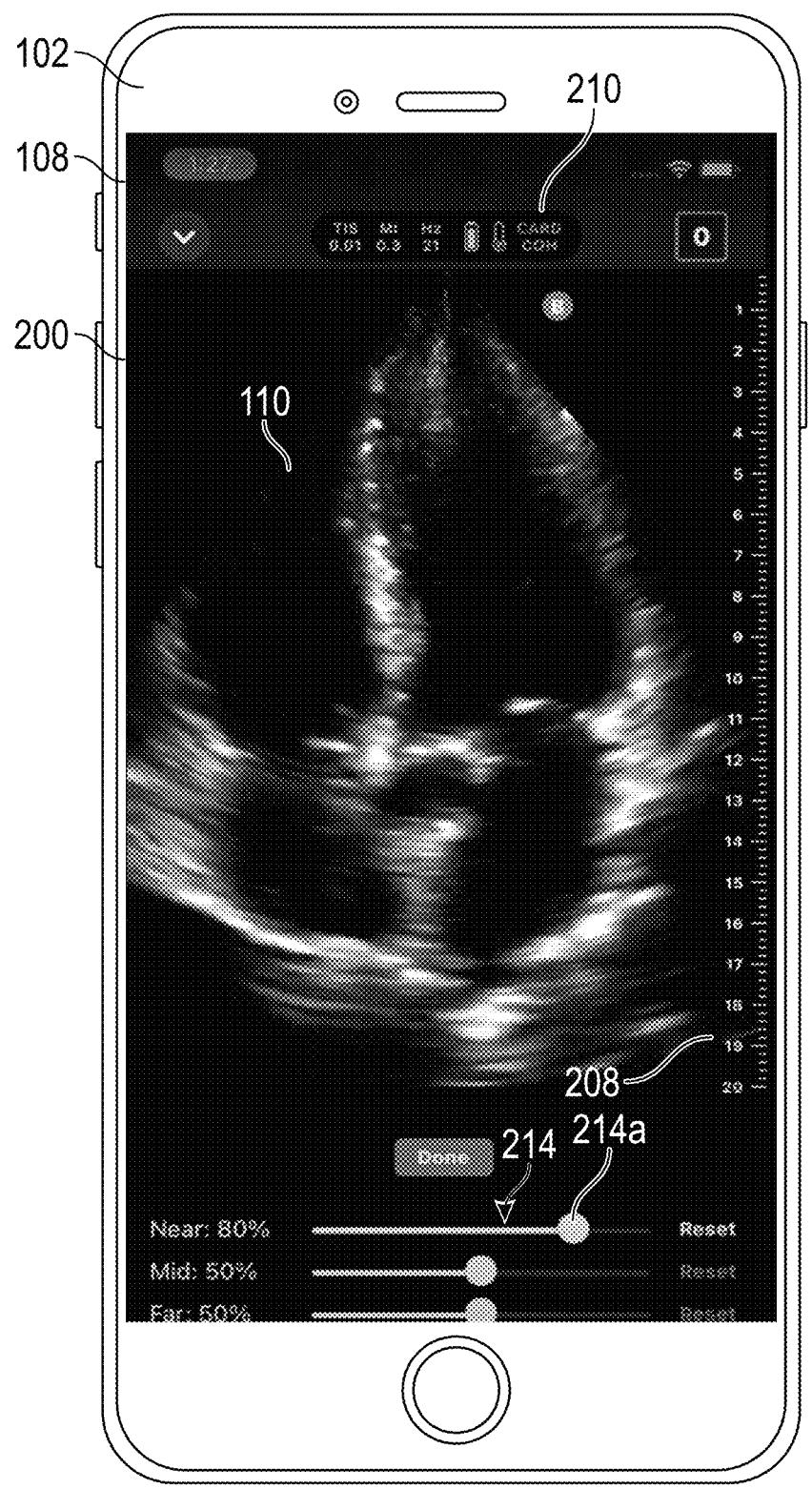
FIG. 16 is a view of the GUI showing adjustment of the TGC settings for the first preset filter after switching from the second preset filter according to one embodiment of the present disclosure.
Figure 17:
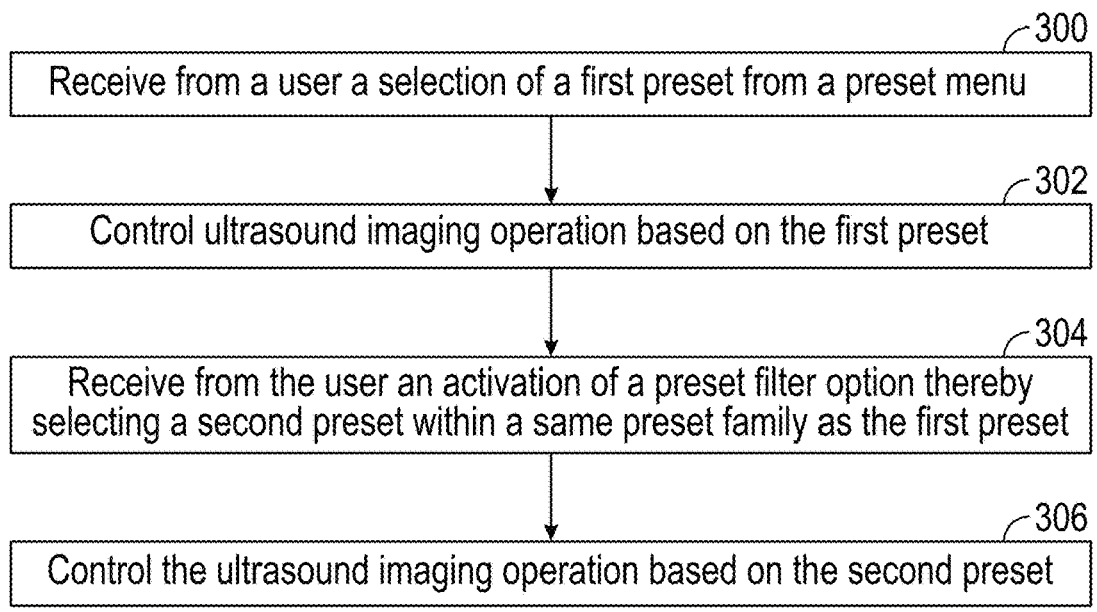
FIGS. 17-20 are flow charts of methods for controlling the processing device of the ultrasound sound system through the GUI according to one embodiment of the present disclosure.

FIGS. 5-16 illustrate graphical user interfaces (GUIs) that may be generated by a processing device 104 (e.g., a smartphone or a tablet) in operative communication with the ultrasound device 102 and displayed by the display screen 108 of the processing device 104, in accordance with certain embodiments described herein. Methods of using the GUI 200, and particular the preset filter option 204, to select presets are shown in FIG. 17, which is described in connection with the GUI 200 of FIGS. 5-16. The methods may be embodied as software instructions executed by the processing device 104 in operative communication with the ultrasound device 102. The processing device 104 processes ultrasound data received from the ultrasound device 102 based on the user-selected presets.

With reference to FIGS. 5-16 the processing device 104 is configured to receive from a user a selection of a first preset 152a from a preset menu 152 using a GUI 200 displayed on the processing device 104 at step 300 of FIG. 17. In the illustrated example of FIG. 5, the user has selected the Cardiac (also known as Cardiac Standard) preset.

Figure 5:
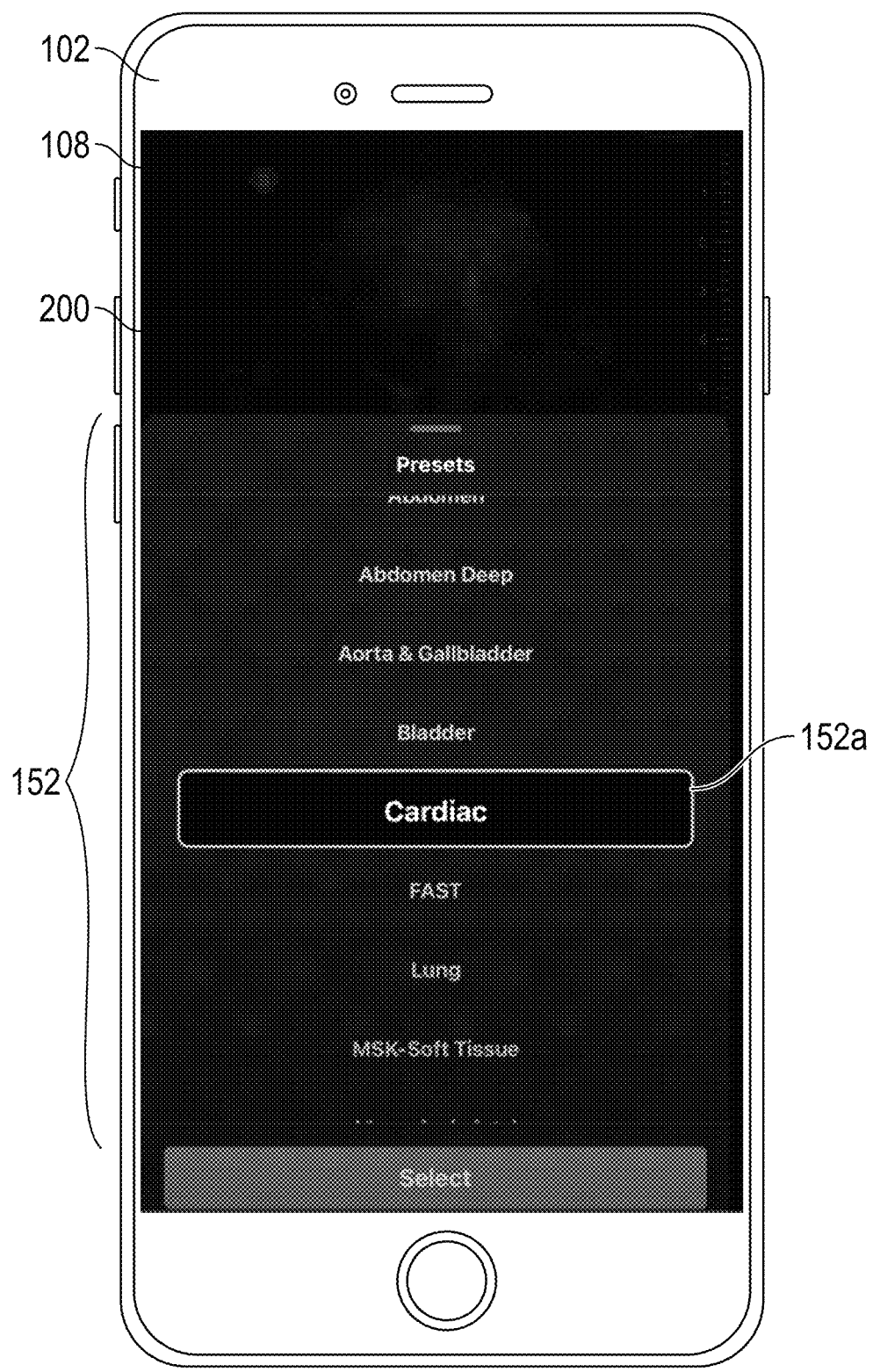
FIG. 5 is a view of a graphical user interface (GUI) displayed on a screen of a processing device of the ultrasound sound system of FIG. 1, the GUI showing a preset menu for selecting a preset or preset family according to one embodiment of the present disclosure.

The GUI 200 may be displayed over a majority of the display screen 108. In embodiments, the GUI 200 may include a preset menu 152 listing the presets. It should be noted that not all of the presets are shown in FIG. 5 since the presets may be arranged in a scrollable list. In embodiments, the presets may be arranged in any other suitable manner (e.g., table of buttons, etc.). The GUI 200 may be activated by the user swiping from an edge (e.g., bottom) of the display screen 108 toward the center. Once activated, the user then selects one of the presets. As described above, the presets may be optimized for imaging a particular type of anatomy and/or for imaging in a particular clinical application, and may also be optimized for human or veterinary imaging. In embodiments, different versions of ultrasound devices 102 may include corresponding menus of presets, such that a human version of the ultrasound devices 102 may list human presets and a veterinary version of the ultrasound devices 102 may list veterinary presets.

At step 302, the processing device 104 controls ultrasound imaging operation based on the selected first preset (in the illustrated example, Cardiac Standard preset). Controlling ultrasound imaging operation may include the processing device controlling ultrasound imaging operation of the ultrasound device and the processing device controlling its own ultrasound imaging operation based on the first preset.

A preset may include values for ultrasound imaging parameters that control ultrasound imaging operations such as transmit, analog processing, digital pre-processing and beamforming, coherent post-processing, and incoherent post-processing. Because some of these ultrasound imaging operations may be performed by the ultrasound device and some may be performed by the processing device, a preset's parameter values may control ultrasound imaging operation of the ultrasound device and the processing device. In other words, the processing device may use a preset to control ultrasound imaging operation of the ultrasound device and its own ultrasound imaging operation. Following are further examples of ultrasound imaging aspects that may be controlled by a preset's parameter values. It should be appreciated that some presets may have values related to more or fewer operations.

Transmit: waveform, voltage, aperture, apodization, focal depth, transmit spacing, transmit span.

Analog processing: amplification, averaging, analog time-gain compensation (TGC), analog to digital conversion.

Digital pre-processing and beamforming: demodulation, digital filtering (e.g., cascaded integrator-comb (CIC) filtering), microbeamforming.

Coherent processing: receive beamforming, transmit beamforming, digital filtering (e.g., finite impulse response (FIR) filtering).

Incoherent processing: Envelope detection, frequency compounding, log compression, spatial filters, gain compensations, scan conversion, gain and dynamic range, image processing The processing device 104 receives selection of the first preset and then transmits commands to the ultrasound device 102 to configure it with parameter values of the first preset. The ultrasound device 102 may use these parameter values when performing ultrasound imaging operations, such as transmit, analog processing, digital pre-processing and beamforming, and coherent processing operations. The processing device 104 thereby controls ultrasound imaging operation of the ultrasound device 102 based on the first preset. Generally, the ultrasound device 102 uses the first preset to collect and process ultrasound data and transmit the ultrasound data back to the processing device 104. The processing device 104 itself may also perform ultrasound imaging operations, such as incoherent processing operations, and may use parameter values of the first preset in such operations. Thus, the processing device 104 may control its own ultrasound imaging operation based on the first preset. When ultrasound images have been generated, the processing device 104 displays the most recent ultrasound image 110 in real time on the display screen 108 of the processing device 104 as shown in FIGS. 6-16 based on the selected preset 152. In embodiments in which the processing device 104 does not perform any ultrasound imaging operation, but merely displays final ultrasound images generated by the ultrasound device 102, the processing device 104 may not itself use a preset.

Figure 6:
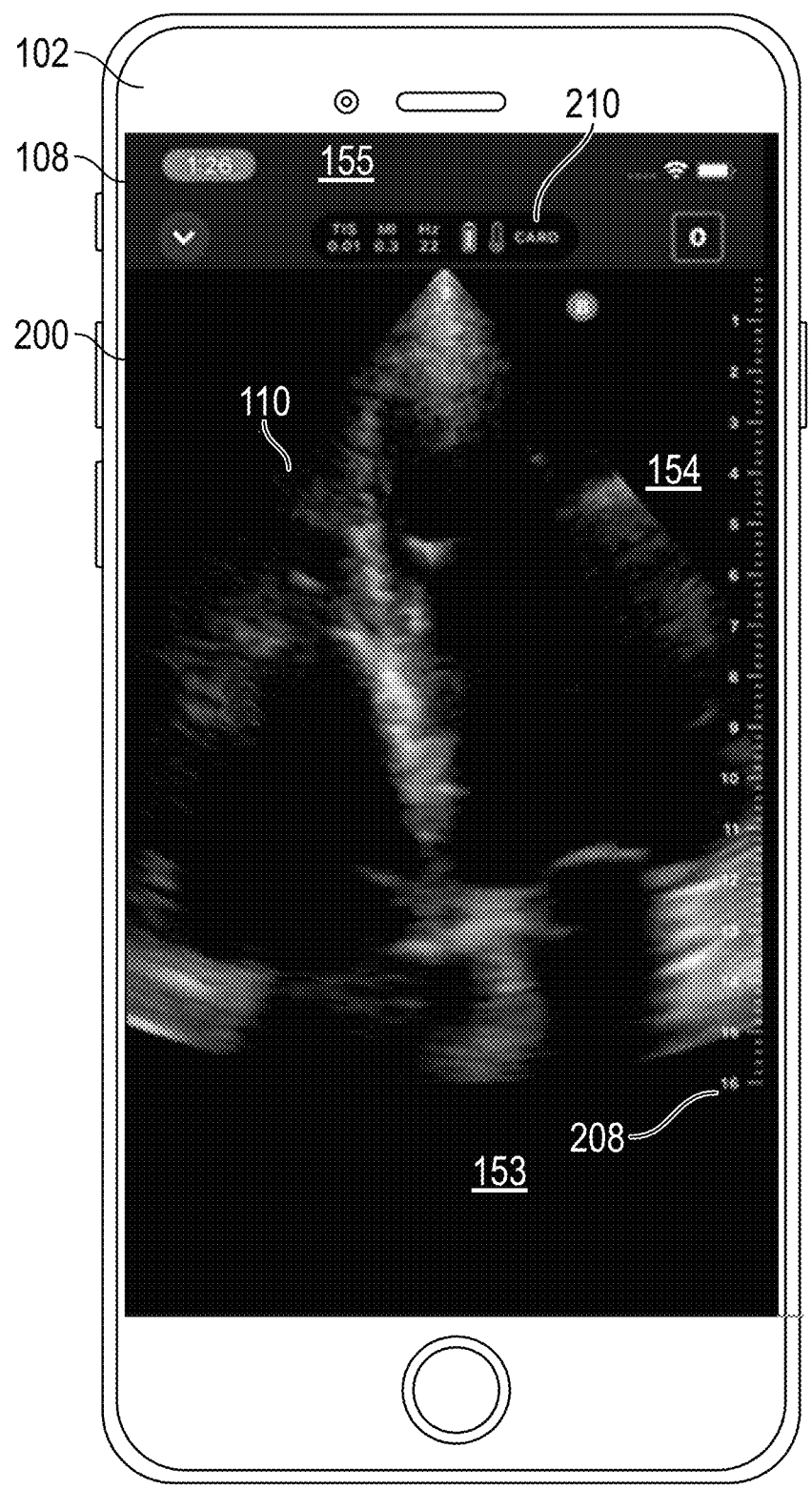
FIG. 6 is a view of the GUI showing an ultrasound image with default imaging depth after selecting the preset according to one embodiment of the present disclosure.
Figure 7:
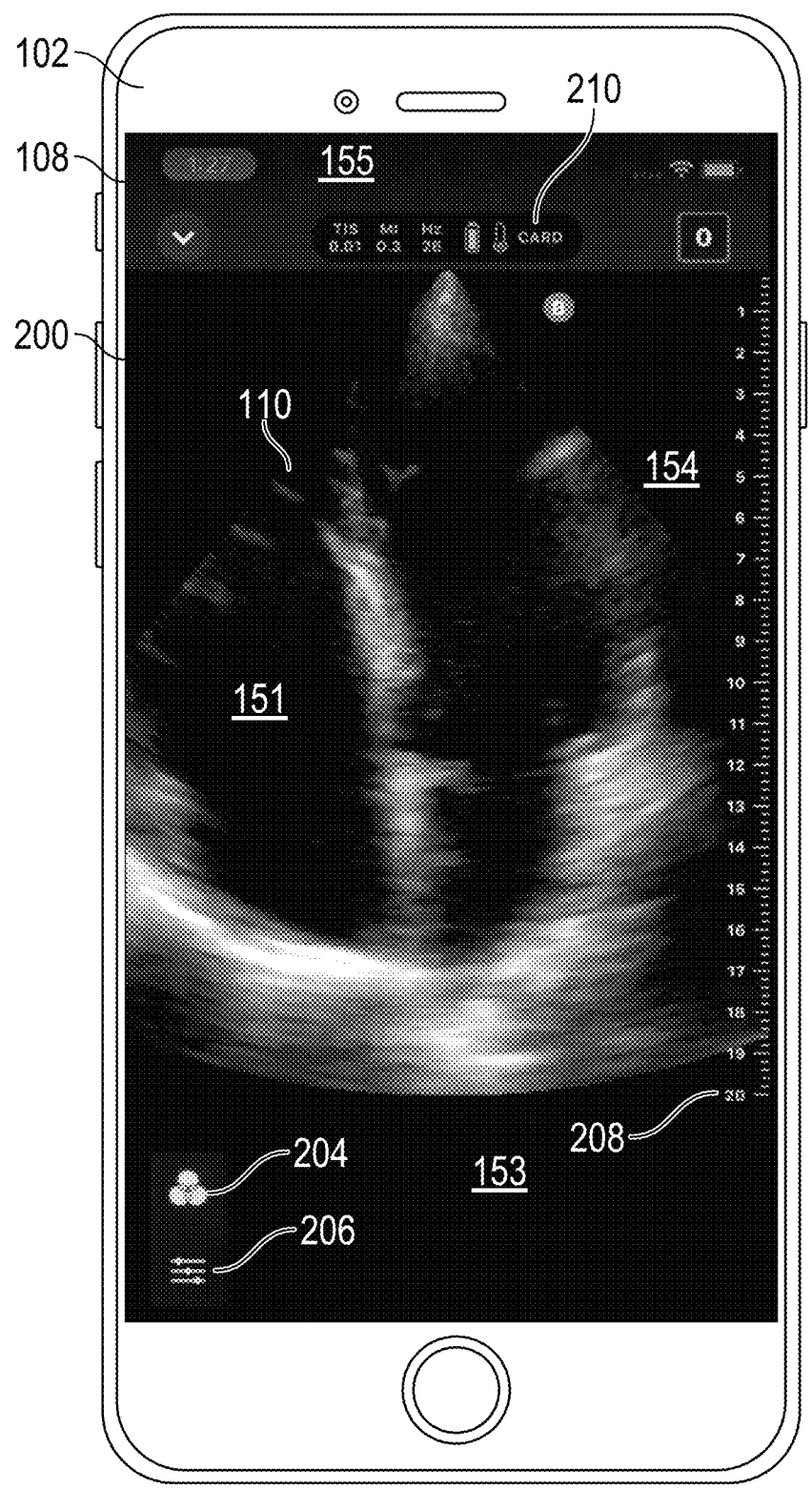
FIG. 7 is a view of the GUI showing an ultrasound image after changing the imaging depth according to one embodiment of the present disclosure.

With reference to FIG. 6, the GUI 200 is shown after selection of the Cardiac (which may also be referred to as Cardiac Standard) preset 152a from the preset menu 152 in FIG. 5. The GUI 200 shows the ultrasound image 110 collected in real time, as well as an imaging depth indicator 208 and a top preset indicator 210. The top preset indicator 210 along with other device status indicators are shown in a fourth region 155 above the first region 151. The top preset indicator 210 indicates that the current preset used for generating the ultrasound images 110 being shown is Cardiac Standard. The default imaging depth may be based on the selected preset, e.g., the Cardiac Standard preset, and may extend to a default depth for the selected preset, e.g., 16 cm. The imaging depth may be displayed by the imaging depth indicator 208 in a third region 154 on a side of the display screen 108 along the side of the first region 151, without obscuring the ultrasound image 110. The user may modify the imaging depth, for example by swiping in a vertical direction across the display screen of the processing device 104. FIG. 7 shows the GUI 200 after the user has changed the imaging depth from the default depth of 16 cm to a new depth of 20 cm. The GUI 200 of FIG. 7 also shows a preset filter option 204 and a time-gain compensation (TGC) option 206, which may appear in the GUI 200 after selection (e.g., tapping) by the user on a particular portion (e.g., a second region 153) of the GUI 200 or generally in a vicinity of the location of the preset filter option 204. The ultrasound image 110 may be shown in a first region 151 of the display screen 108, and the preset filter option 204 and the TGC option 206 may be shown in the second region 153, which may be below the first region 151, without obscuring the ultrasound image 110.

A preset family includes related presets that are grouped together. Certain presets within a family may be optimized for imaging the same anatomy or the same anatomical region or the same type of anatomy, but may differ in certain ways. For example, one preset family may have a standard preset and a deep preset, both optimized for imaging the same anatomy. As a specific example, a preset family may include an abdomen preset and an abdomen deep preset, where both presets are optimized for imaging the abdomen, but the abdomen preset is optimized for standard patients and the abdomen deep preset is optimized for technically challenging patients, such as those with high BMI or those with highly attenuating livers, as in hepatitis. As another example, one preset family may have a harmonics preset and a fundamentals preset, both optimized for imaging the same anatomy. As a specific example, a preset family may include a cardiac:harmonics preset and a cardiac:fundamentals preset, where both presets are optimized for imaging the heart, but one preset uses harmonic frequencies and one preset uses fundamental frequencies. As another example, one preset family may have an OB 1/GYN preset and an OB 2/3 preset, where both presets are optimized for obstetric applications, but one preset is optimized for use in the first month of pregnancy and the other preset is optimized for use in the second and third months of pregnancy.

Examples preset families for human ultrasound imaging include:
  Cardiac: Cardiac Standard, Cardiac Coherence, and Cardiac Deep;
  Abdomen: Abdomen, Abdomen Deep, Aorta & Gallbladder;
  MSK: MSK, MSK-Soft Tissue, Small Organ;
  OB/GYN: OB 1/GYN, OB 2/3;
  Vascular: Vascular: Access, Vascular: Carotid, Others;
  Cardiac: Cardiac Harmonics, Cardiac Fundamentals;
  Abdomen: Abdomen Harmonics, Abdomen Fundamentals; and
  Lung: Lung: Artifacts, Lung: Consolidation, Lung: Tissue.

Examples preset families for veterinary ultrasound imaging include:
  Cardiac Harmonics: Cardiac Harmonics, Cardiac Standard;
  Cardiac Deep Harmonics: Cardiac Deep, Cardiac Deep Harmonics;
  Abdomen: Abdomen, Abdomen Deep;
  MSK (Musculoskeletal): MSK, and may be Small Organ;
  Vascular: Vascular: Access, Vascular: Carotid, Others;
  Cardiac: Cardiac Harmonics, Cardiac Fundamentals; and
  Abdomen: Abdomen Harmonics, Abdomen Fundamentals.

It should be appreciated that a preset family need not include every preset in a particular group above; a preset family may include a subset of two or more of the presets listed in a particular group above. For example, a preset family for cardiac imaging may just include Cardiac Standard and Cardiac Deep presets.

For further description of the Cardiac Coherence preset see U.S. patent application Ser. No. 17/525,791 titled "METHODS AND SYSTEMS FOR COHERENCE IMAGING IN OBTAINING ULTRASOUND IMAGES," filed Nov. 12, 2021, the entire disclosure of which is incorporated by reference herein in its entirety.

When the preset selected from the preset menu 152 of FIG. 5 is part of a family of related presets, the preset filter option 204 may be displayed in the GUI 200. (As described above, in some embodiments the preset filter option 204 may be hidden until the user taps a particular portion of the GUI 200). The preset filter option 204 allows the user to select from a plurality of (e.g., two, three, or more) presets within the family of the preset originally selected from the preset menu 152 of FIG. 5. In some embodiments, repeated activation of the preset filter option 204 may cycle through the presets within the preset family. In the illustrated example, the user has selected the Cardiac Standard preset 152a from the preset menu 152. This preset is part of the preset family that includes Cardiac Standard, Cardiac Coherence, and Cardiac Deep. Repeated selection of the preset filter option 204 may cause the preset to cycle from Cardiac Standard to Cardiac Coherence, from Cardiac Coherence to Cardiac Deep, from Cardiac Deep to Cardiac Standard, etc.

It should be appreciated that the number of presets which may be selected using the preset filter option 204 may be smaller than the number of presets which may be selected from preset menu in the GUI 200 of FIG. 5.

In some embodiments, a subset of the presets displayed as options by the preset menu 152 in FIG. 5 may not be in preset families. For example, the bladder preset may not be part of a preset family. Upon receiving from the user a selection of such a preset from the preset menu 152 of FIG. 5, the processing device 104 would not display the preset filter option 204. (As described above, in some embodiments the preset filter option 204 may be hidden until the user taps a particular portion of the GUI 200. In such embodiments, when the user selects from the preset menu 152 a preset that is not in a family, the preset filter option 204 may not appear even when the user taps the particular portion of the GUI 200.)

In some embodiments, a subset of (i.e., not all) available presets may be displayed in the preset menu 152 of FIG. 5. For example, the Cardiac Coherence preset may not be displayed in the preset menu 152 of FIG. 5. To select the Cardiac Coherence preset, the user may select the Cardiac Standard preset from the preset menu 152 of FIG. 5 and then use the preset filter option 204 to cycle to the Cardiac Coherence preset.

In some embodiments, more than one preset within a family may be displayed in the preset menu 152 of FIG. 5. For example, both the Abdomen preset and the Aorta & Gallbladder preset may be part of a preset family, and both presets may be displayed in the preset menu 152 of FIG. 5. To select, for example, the Aorta & Gallbladder preset, the user could select the Aorta & Gallbladder preset from the preset menu 152 of FIG. 5, or the user could select the Abdomen preset from the preset menu 152 of FIG. 5 and then use the preset filter option 204 to select the Aorta & Gallbladder preset.

Figure 8:
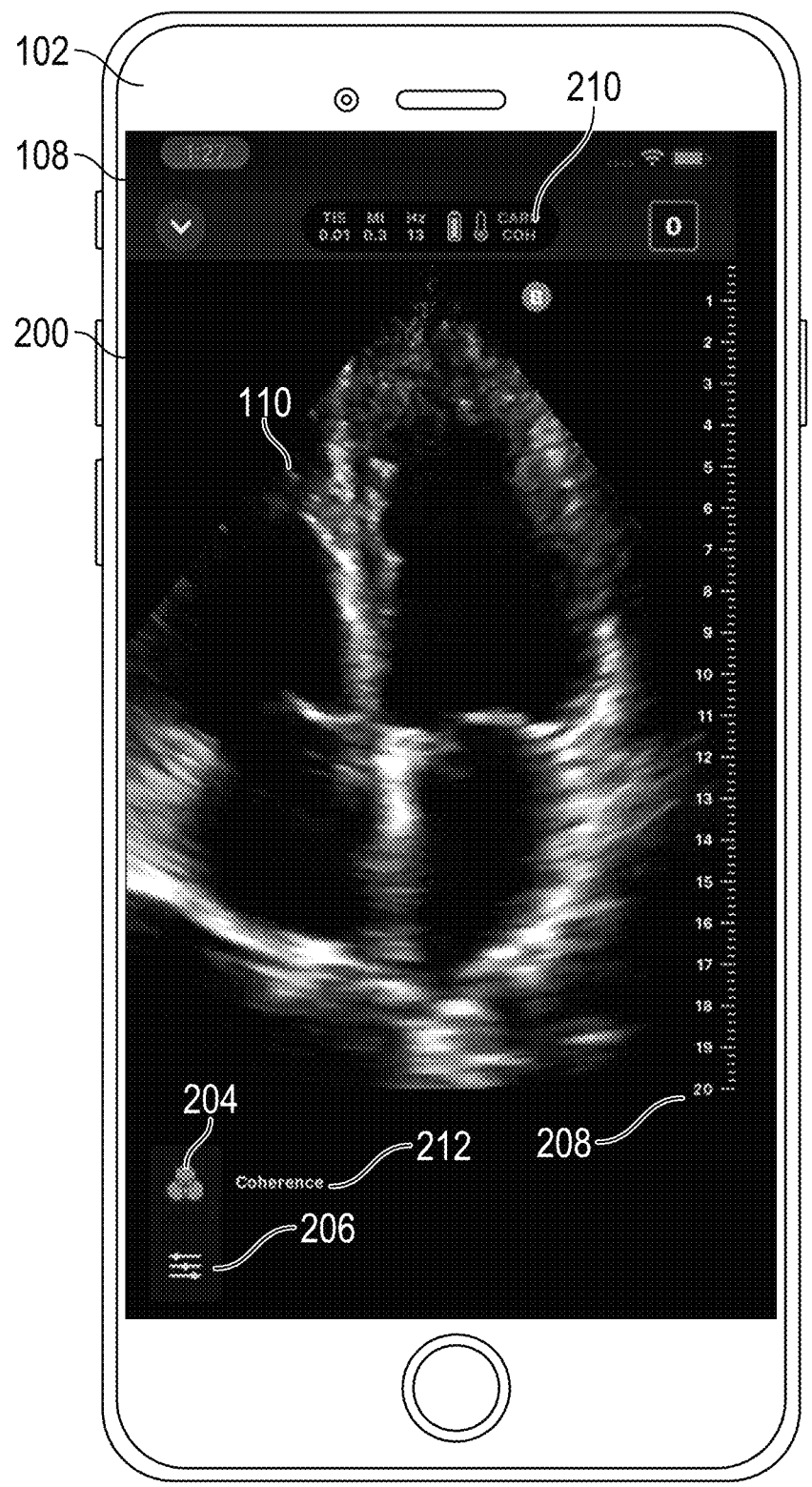
FIG. 8 is a view of the GUI showing selection of a first preset filter and a first preset indicator according to one embodiment of the present disclosure.
Figure 9:
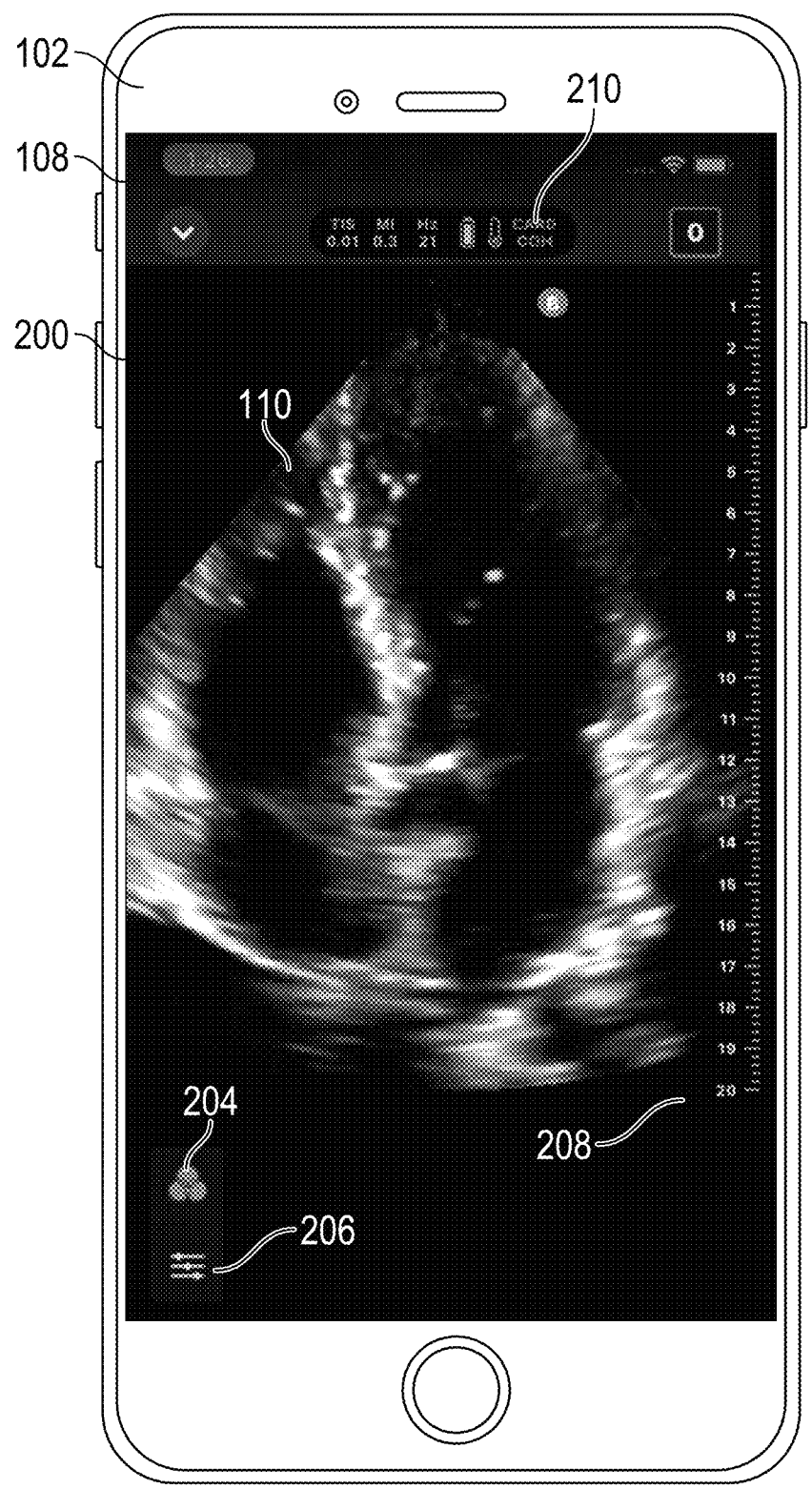
FIG. 9 is a view of the GUI showing the ultrasound image after selection of the first preset filter according to one embodiment of the present disclosure.

At step 304, the processing device 104 receives from the user an activation of the preset filter option 204 displayed by the processing device 104, thereby selecting a second preset (in the illustrated example of FIG. 8, the Cardiac Coherence preset) within the same preset family as the first preset. In other words, activation of the preset filter option 204 is the manner in which the user selects the second preset. Thus, the preset is changed from the first preset to the second preset. At step 306, the processing device 104 controls ultrasound imaging operation based on the selected second preset, in the same manner as described above with reference to the first preset at step 302. FIG. 8 shows the GUI 200 that is shown after selection of the preset filter option 204 from the GUI 200 in FIG. 7. Selection of the preset filter option 204 switches the current preset used for generating the ultrasound images 110 from Cardiac Standard to Cardiac Coherence. This GUI includes a side preset indicator 212 indicating that the new preset is Cardiac Coherence. The top preset indicator 210 also indicates that that the current preset is Cardiac Coherence. After activating the preset filter option 204, the side preset indicator 212 may disappear after a preset period of time, e.g., 5 seconds, to avoid cluttering of the GUI 200, as shown in FIG. 9.

It should be noted that the imaging depth remains the same as it was prior to selection of the preset filter option 204, namely 20 cm, even though the default imaging depth for the Cardiac Coherence preset is 16 cm. In other words, imaging depth persists even when different presets are selected by the user using the preset filter option 204. This allows the user to more easily compare ultrasound images 110 generated using a previously selected preset versus ultrasound images 110 generated using a currently selected preset.

Figure 18:
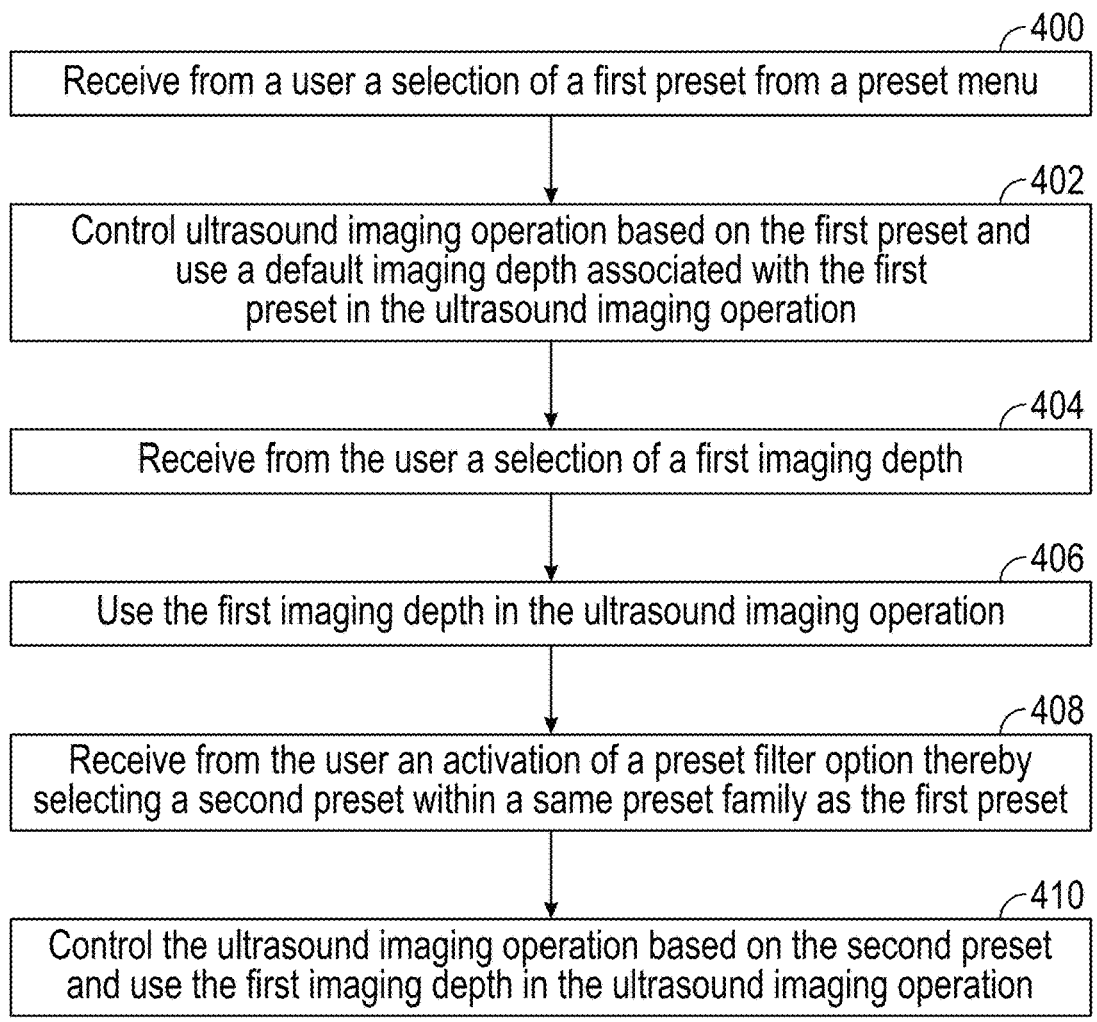

The method by which imaging depth is used by the processing device 104 when presets are selected by a user using the GUI 200, and particularly the preset filter option 204, is shown in FIG. 18. The method of FIG. 18 may be an embodiment of the method of FIG. 17 with the addition of certain features.

At step 400, the processing device 104 receives from a user a selection of a first preset from the preset menu 152 displayed by the processing device 104. Step 400 may be the same as step 300. For example, in FIG. 5 the user selects the Cardiac Standard preset (the first preset). At step 402, the processing device 104 controls ultrasound imaging operation based on the first preset and uses a default imaging depth associated with the first preset in the ultrasound imaging operation. Step 402 may be the same as step 302, with the additional feature that a default imaging depth associated with the first preset is used. For example, in FIG. 6, the default imaging depth or the first preset is 16 cm. In some embodiments, imaging depth may be a parameter used just by the processing device 104 in its ultrasound imaging operations (i.e., processing ultrasound data, generating ultrasound images, and/or displaying ultrasound images). In some embodiments, imaging depth may be a parameter used just by the ultrasound device 102 in its ultrasound imaging operations (i.e., collecting ultrasound data, processing ultrasound data, and/or generating ultrasound images). In some embodiments, imaging depth may be a parameter used by both the processing device 104 and the ultrasound device 102. In embodiments in which the ultrasound device 102 uses the imaging depth parameter, the processing device 104 may transmit an indication of this parameter to the ultrasound device 102. At step 404, the processing device 104 receives from the user a selection of a first imaging depth, and at step 406, the processing device 104 uses the first imaging depth in the ultrasound imaging operation. For example, in FIG. 7, the user has selected a new imaging depth (i.e., the first imaging depth) of 20 cm, and this imaging depth is used for continued imaging with the Cardiac Standard preset (i.e., the first preset). The first imaging depth is different from the default imaging depth associated with the first preset. At step 408, the processing device 104 receives from the user an activation of the preset filter option 204 thereby selecting a second preset within a same preset family as the first preset. Step 408 may be the same as step 304. For example, in FIG. 8, the user has activated the preset filter option 204 to select the Cardiac Coherence preset (i.e., the second preset). At step 410, the processing device 104 controls the ultrasound imaging operation based on the second preset and uses the first imaging depth in the ultrasound imaging operation. Further description of using an imaging depth may be found with reference to step 402. The first imaging depth may be different than the default imaging depth associated with the second preset. For example, in FIG. 8, the imaging depth remains 20 cm (i.e., the first imaging depth), which is the imaging depth used during use of the Cardiac Standard preset just prior to the switch to the Cardiac Coherence preset (i.e., at step 406), even though the default imaging depth for the Cardiac Coherence preset is 16 cm. The processing device 104 may automatically set the imaging depth at the first imaging depth, rather than the default imaging depth associated with the second preset, without any user input to do so between step 408 and step 410.

While imaging depth may persist even when different presets are selected using the preset filter option 204, other parameters such as time-gain compensation (TGC) may not persist. TGC is used to adjust gain in an ultrasound image as a function of depth. In the ultrasound signal, a signal that arrives at a deeper region of the subject and returns is weaker. Therefore, an ultrasound image of a deep region may be relatively dark and unclear. The ultrasound system can compensate for this by modulating the relative gain for signals arriving from different regions (i.e., signals that arrive at different times).

Figure 19:
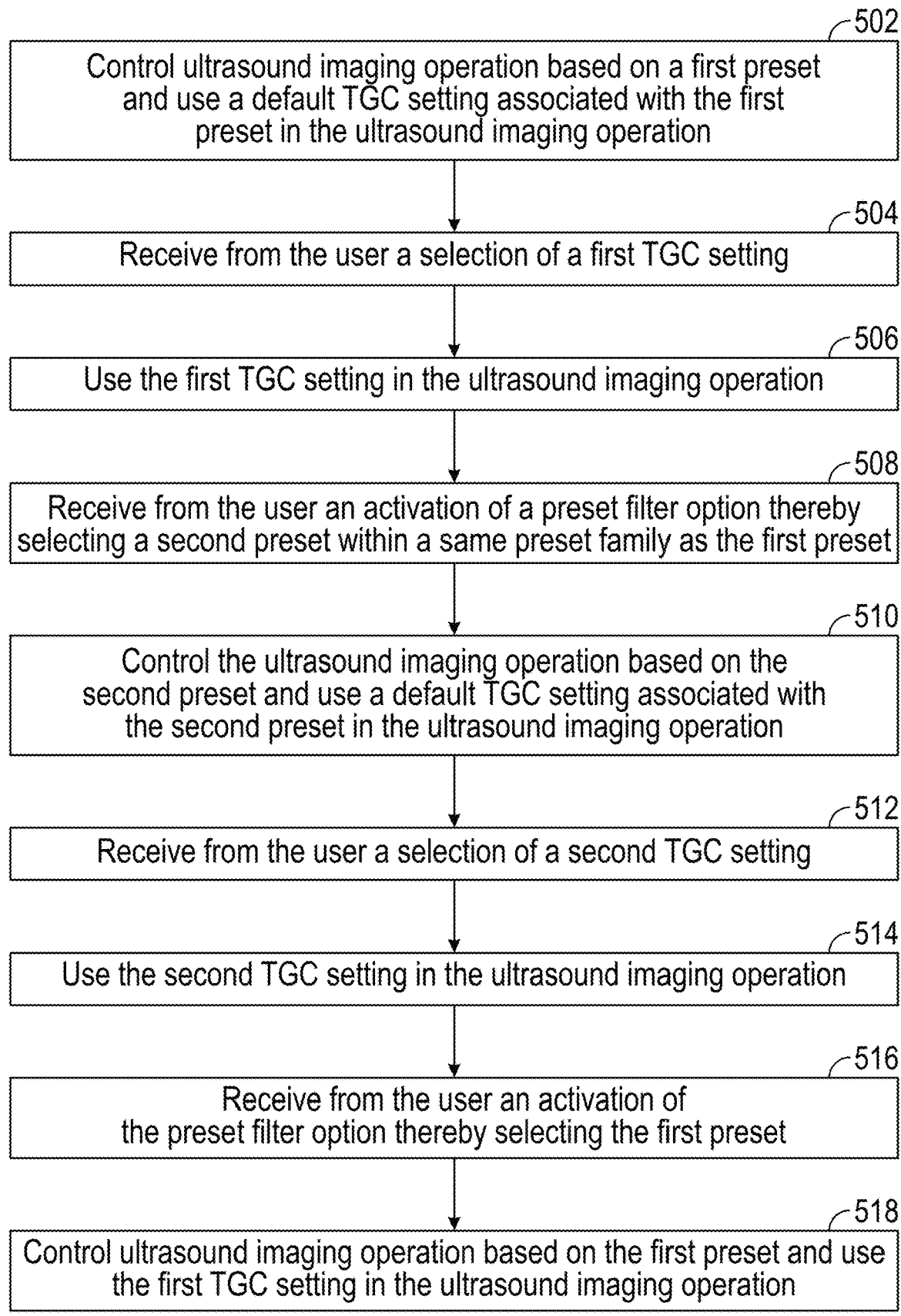

The method by which TGC is used by the processing device 104 when presets are selected by a user using the GUI 200, and particularly the preset filter option 204, is shown in FIG. 19. The method of FIG. 19 may be an embodiment of the method of FIG. 17 with the addition of certain features.

Figure 10:
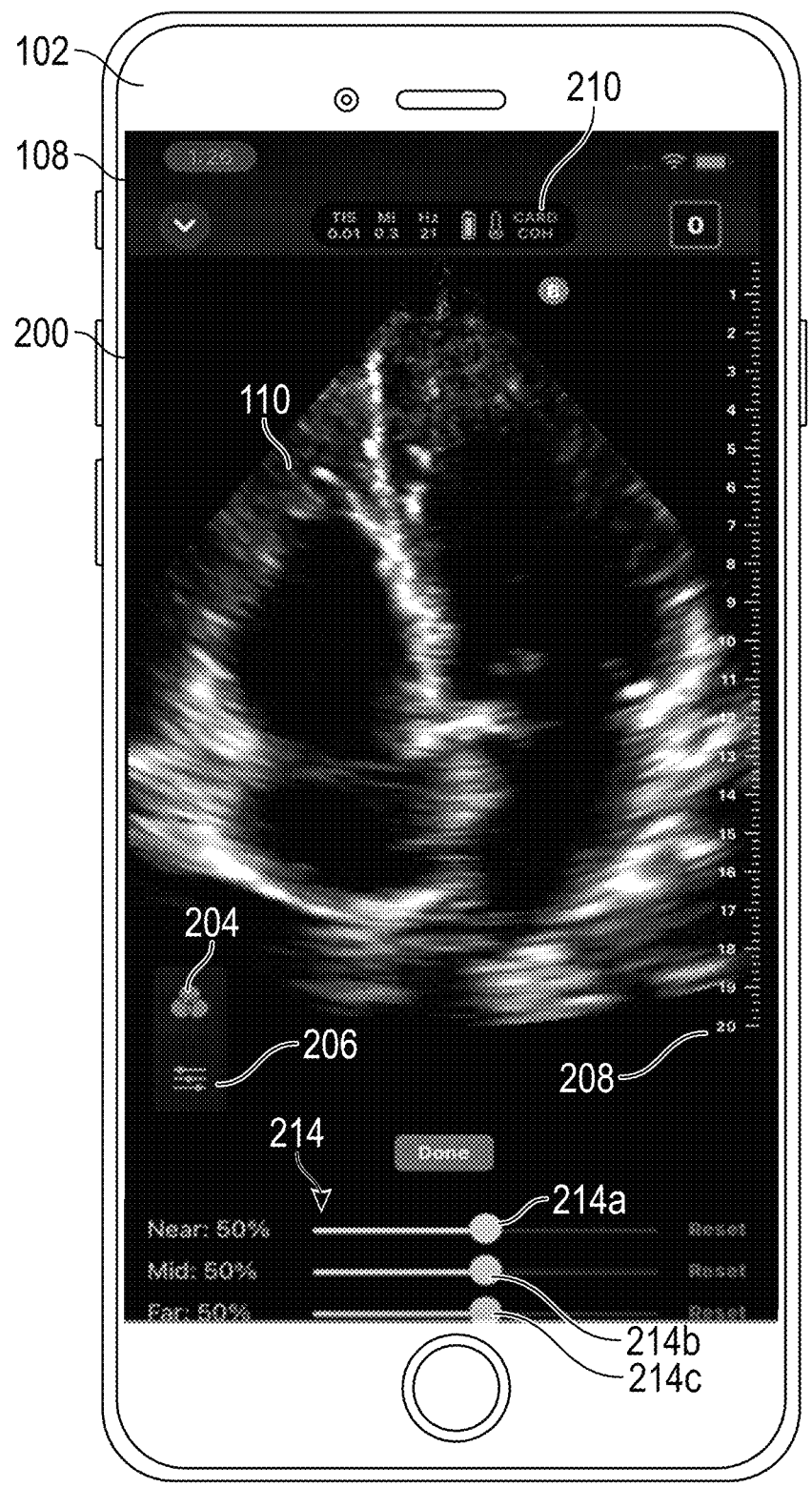
FIG. 10 is a view of the GUI showing time-gain compensation (TGC) settings for the first preset filter according to one embodiment of the present disclosure.

At step 502, the processing device 104 controls ultrasound imaging operation based on a first preset and uses a default TGC setting associated with the first preset in ultrasound imaging operation. (As referred to herein, "TGC setting" may refer to a collection of multiple settings for different depth regions.) Step 502 may be the same as step 302, with the additional feature that a default TGC setting associated with the first preset is used. In some embodiments, a TGC setting may be a parameter used just by the processing device 104 in its ultrasound imaging operations (i.e., processing ultrasound data, generating ultrasound images, and/or displaying ultrasound images). In some embodiments, a TGC setting may be a parameter just used by the ultrasound device 102 in its ultrasound imaging operations (i.e., collecting ultrasound data, processing ultrasound data, and/or generating ultrasound images). In some embodiments, a TGC setting may be a parameter used by both the processing device 104 and the ultrasound device 102. In embodiments in which the ultrasound device 102 uses the imaging depth parameter, the processing device 104 may transmit an indication of this parameter to the ultrasound device 102. As shown in FIG. 10, upon selecting the TGC option 206, TGC settings 214 are displayed, which include a plurality of sliders 214a-c (e.g., near, mid, far) for adjusting multiple TGC parameters. Each of the sliders 214a-c may be individually adjusted. TGC is used to adjust a gain of the depth of the ultrasound image 110. In embodiments, the TGC settings 214 may include any suitable number of sliders or any other GUI element, e.g., text box, drop down menu, etc. In the example of FIG. 10, the default TGC setting for the Cardiac Coherence preset (i.e., the first preset) is 50%/50%/50% for Near/Mid/Far.

Figure 11:
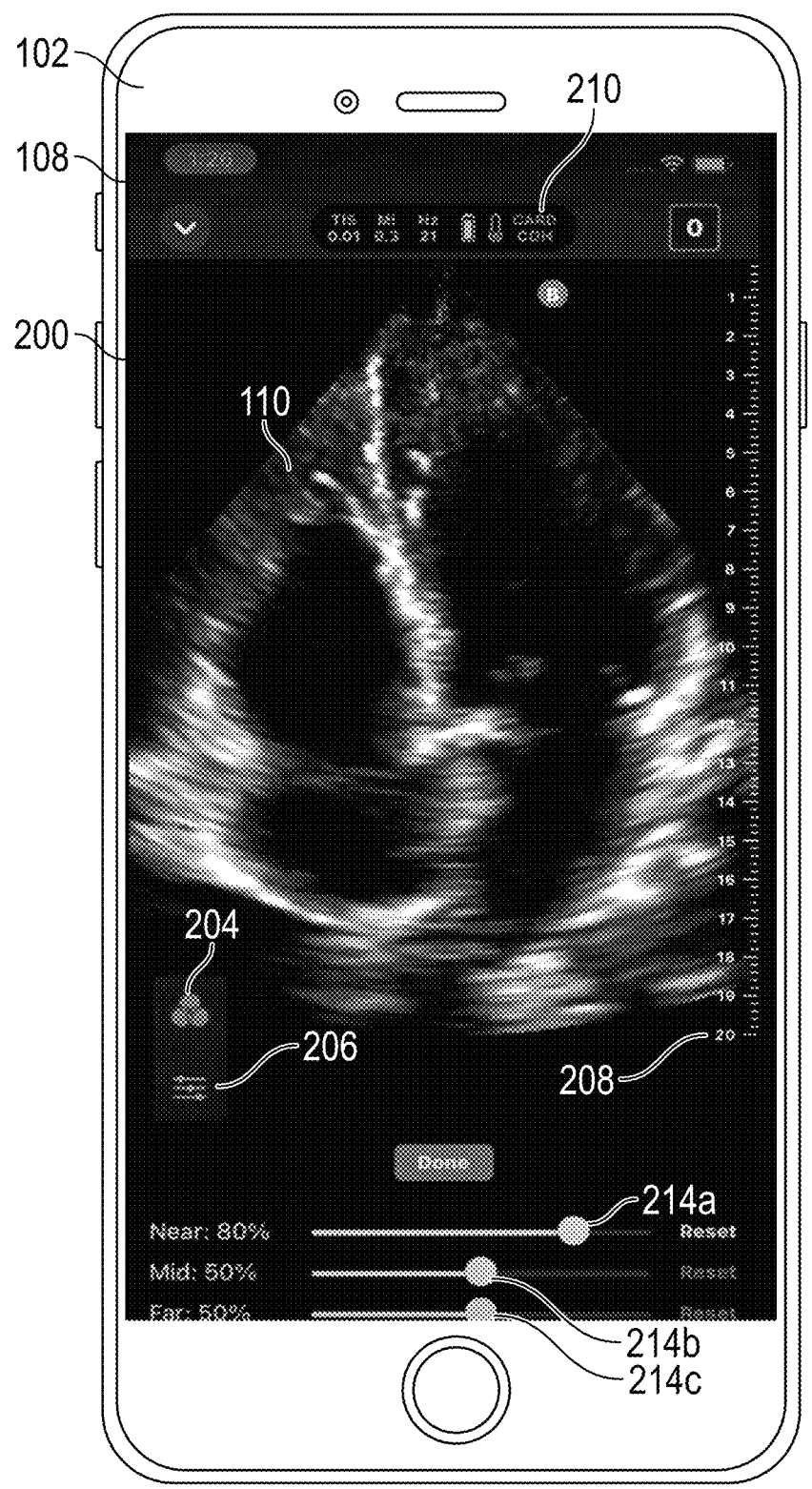
FIG. 11 is a view of the GUI showing adjustment of the TGC settings for the first preset filter according to one embodiment of the present disclosure.
Figure 12:
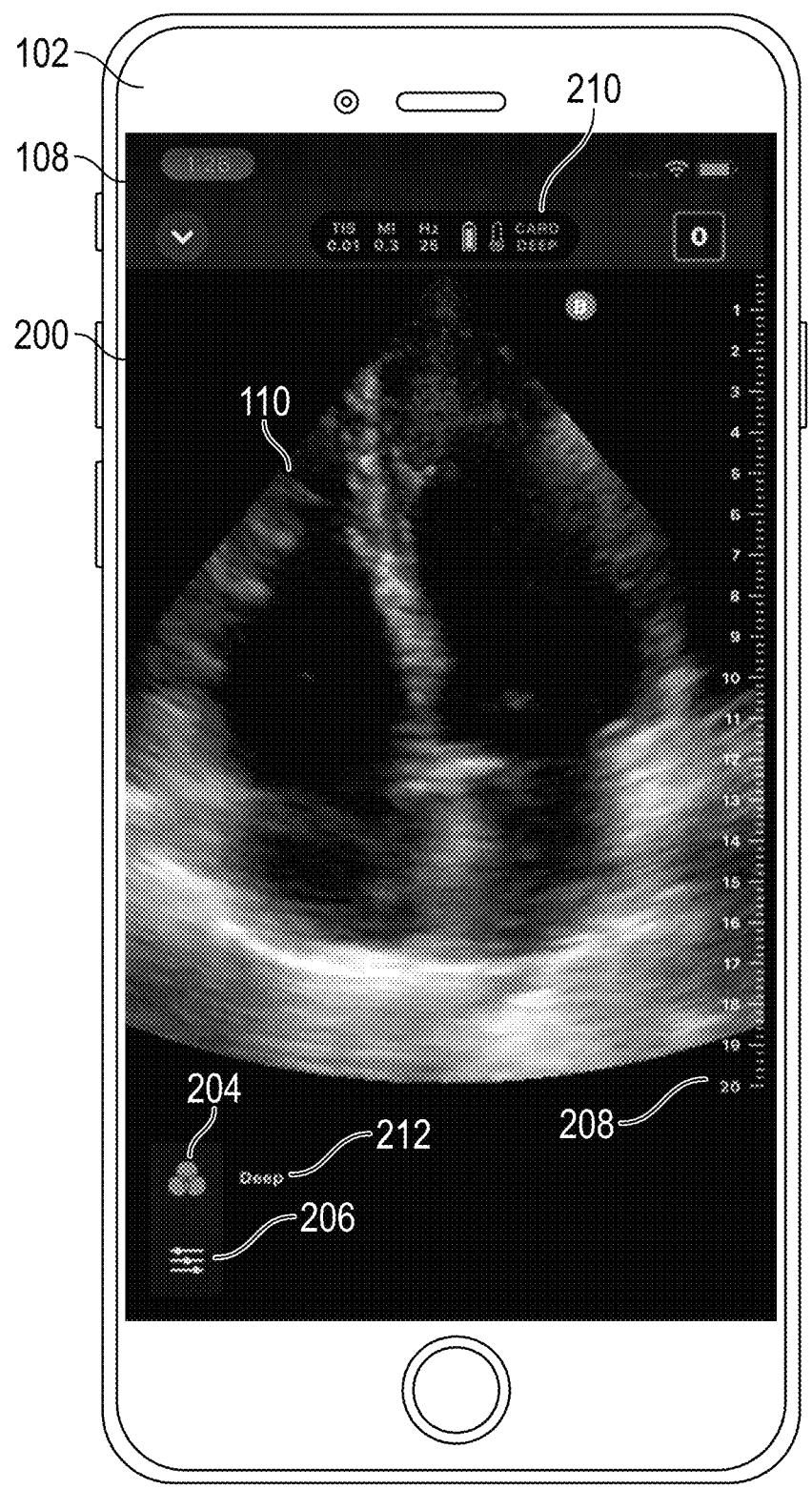
FIG. 12 is a view of the GUI showing selection of a second preset filter and a second preset indicator according to one embodiment of the present disclosure.

At step 504, the processing device 104 receives from the user a selection of a first TGC setting, and at step 506, the processing device 104 uses the first TGC setting in the ultrasound imaging operation. For example, FIG. 11 shows the GUI 200 after modification of the TGC settings 214 by the user, and in particular by moving the near slider 214a. The default TGC setting associated with the first preset may be different than the first TGC setting. Here, the user has modified the settings from the default of 50%/50%/50% to 80%/50%/50% (i.e., the first TGC setting) for Near/Mid/Far.

Figure 13:
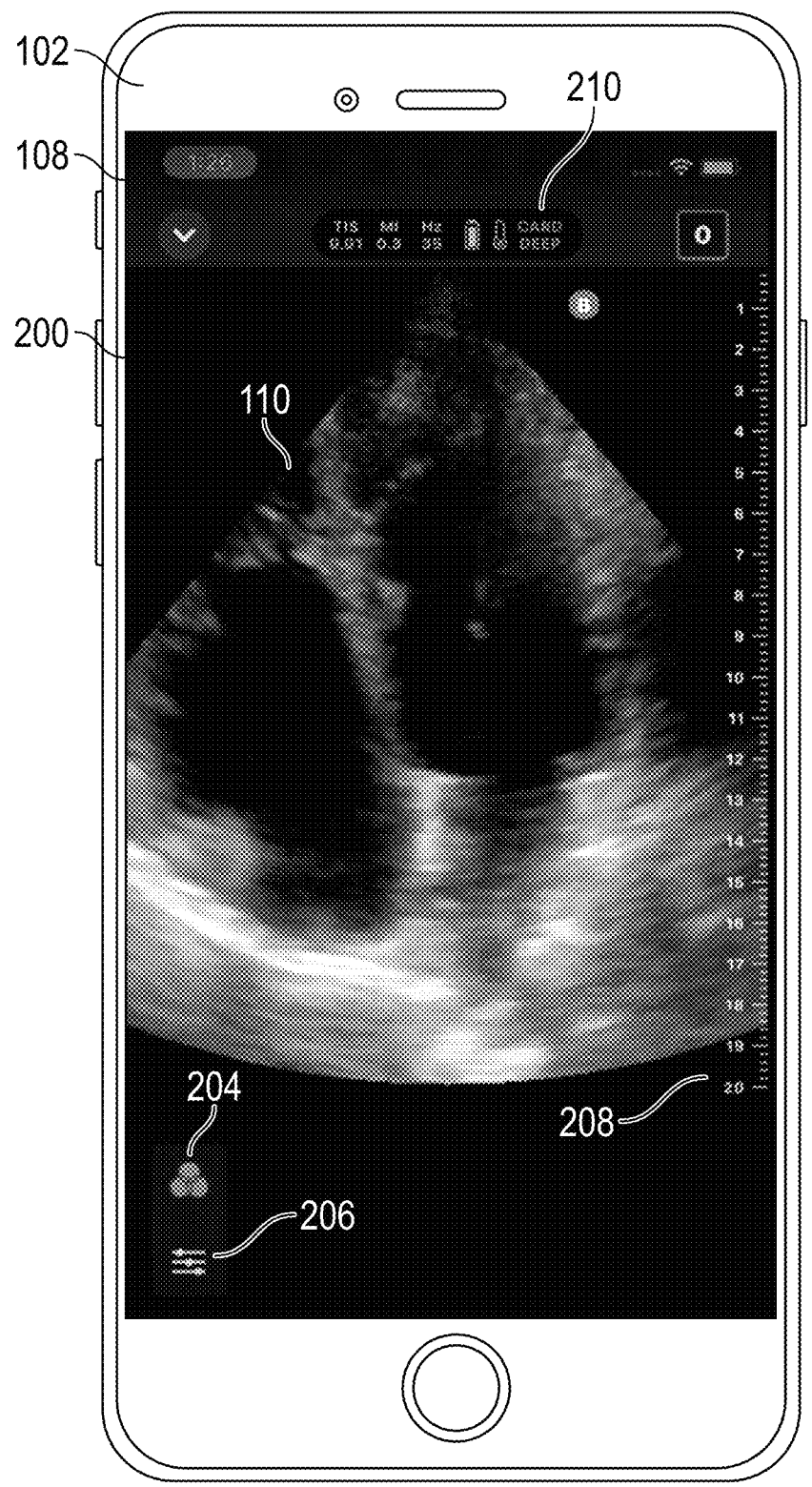
FIG. 13 is a view of the GUI showing the ultrasound image after selection of the second preset filter according to one embodiment of the present disclosure.
Figure 14:
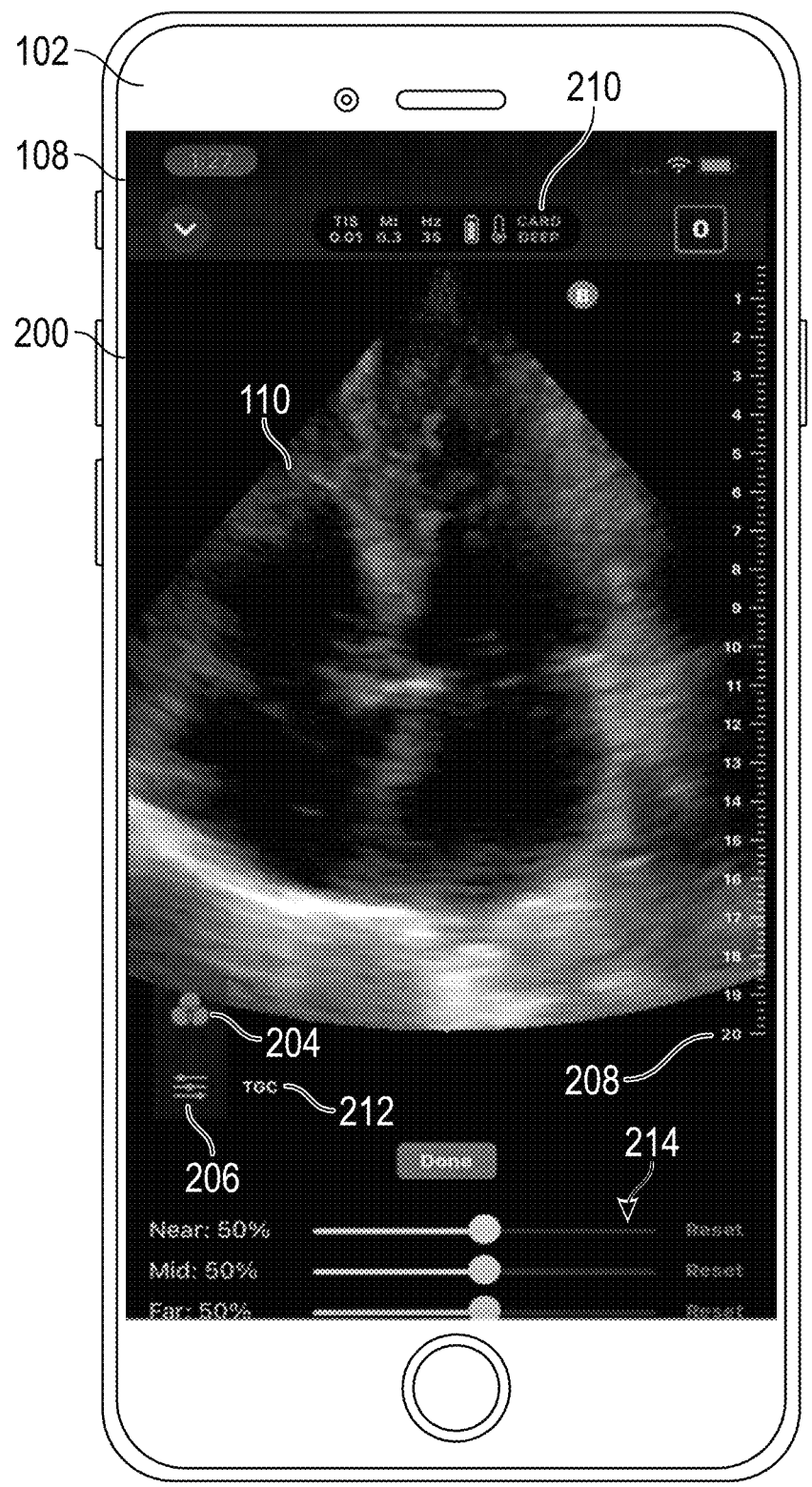
FIG. 14 is a view of the GUI showing the TGC settings for the second preset filter according to one embodiment of the present disclosure.

At step 508, the processing device 104 receives from the user an activation of the preset filter option 204 thereby selecting a second preset within a same preset family as the first preset. Step 508 may be the same as step 304. For example, in FIG. 12, the user has activated the preset filter option 204 to select the Cardiac Deep preset (i.e., the second preset). After selecting the preset filter option 204, the side preset indicator 212 may disappear after a preset period of time, e.g., 5 seconds, to avoid cluttering of the GUI 200, as shown in FIG. 13. The processing device 104 may save the most-recently used TGC setting for the first preset for later use. In the illustrated example, the processing device 104 may save the TGC setting 80%/50%/50% and associated it with the Cardiac Coherence for later use. This saving may occur continuously whenever a new TGC setting is selected (e.g., at steps 504 and 506) or only when the preset filter option 204 is activated (e.g., at step 508). In other words, the saving may occur prior to or upon activation of the preset filter option 204. At step 510, the processing device 104 controls the ultrasound imaging operation based on the second preset and uses a default TGC setting associated with the second preset in the ultrasound imaging operation. Further description of using a TGC setting may be found with reference to step 502. The default TGC setting associated with the second preset may be different than the first TGC setting. In the example of FIG. 14, although the TGC settings were most recently modified to 80%/50%/50%, while in the Cardiac Coherence preset, the settings have reverted to the default settings for Cardiac Deep, i.e., 50%/50%/50% for Near/Mid/Far, following the switching of the preset from Cardiac Coherence to Cardiac Deep. The processing device 104 may automatically set the TGC setting to be the default TGC setting associated with the second preset without any user input to do so between step 508 and step 510.

At step 512, the processing device 104 receives from the user a selection of a second TGC setting, and at step 514, the processing device 104 uses the second TGC setting in the ultrasound imaging operation. For example, FIG. 15 shows the GUI 200 after modification of the TGC settings 214 by the user. The default TGC setting associated with the second preset may be different than the second TGC setting. The second TGC setting may also be different than the first TGC setting Here, the user has modified the settings from the default of 50%/50%/50% to 62%/50%/24% (i.e., the second TGC setting) for Near/Mid/Far. At step 516, the processing device 104 receives from the user an activation of the preset filter option 204 thereby selecting the first preset. For example, in FIG. 16, the user has activated the preset filter option 204 to cycle back to the Cardiac Coherence preset. In the illustrated example, in which the preset family may include the Cardiac Standard, Cardiac Coherence, and Cardiac Deep presets, the user may select the preset filter option 204 twice to switch from Cardiac Deep to Cardiac Standard and then from Cardiac Standard to Cardiac Coherence due to the cyclical behavior of the preset filter option 204.

At step 518, the processing device 104 controls the ultrasound imaging operation based on the first preset and uses the first TGC setting in the ultrasound imaging operation. As noted above, the processing device 104 may save certain settings, such as TGC settings, that were selected when a specific preset was selected. Thus, once the user activates the preset filter option 204 to cycle back to the Cardiac Coherence preset (i.e., the first preset), the processing device 104 automatically retrieves the saved TGC settings that were most recently used in the Cardiac Coherence preset (at step 506), namely 80%/50%/50% (the first TGC setting), as shown in FIG. 16. The TGC settings used are those that were most recently set while in the Cardiac Coherence, even though the user has, since then, switched to other presets and modified the TGC settings while in those presets. For example, the user most recently switched the TGC setting to 62%/50%/24% when in the Cardiac Deep preset, and yet instead the processing device 104 automatically applies the TGC setting 80%/50%/50% most recently used when in the Cardiac Coherence preset. The processing device 104 may automatically set the TGC setting to be the first TGC setting without any user input to do so between step 516 and step 518. Thus, it should be appreciated that when the user has most recently selected a TGC setting different than the default TGC setting associated with a particular preset, the processing device 104 may save this TGC setting, and when the user cycles back to that preset, the processing device 104 may immediately use the saved user-selected TGC setting rather than the default TGC setting for that preset.

Figure 20:
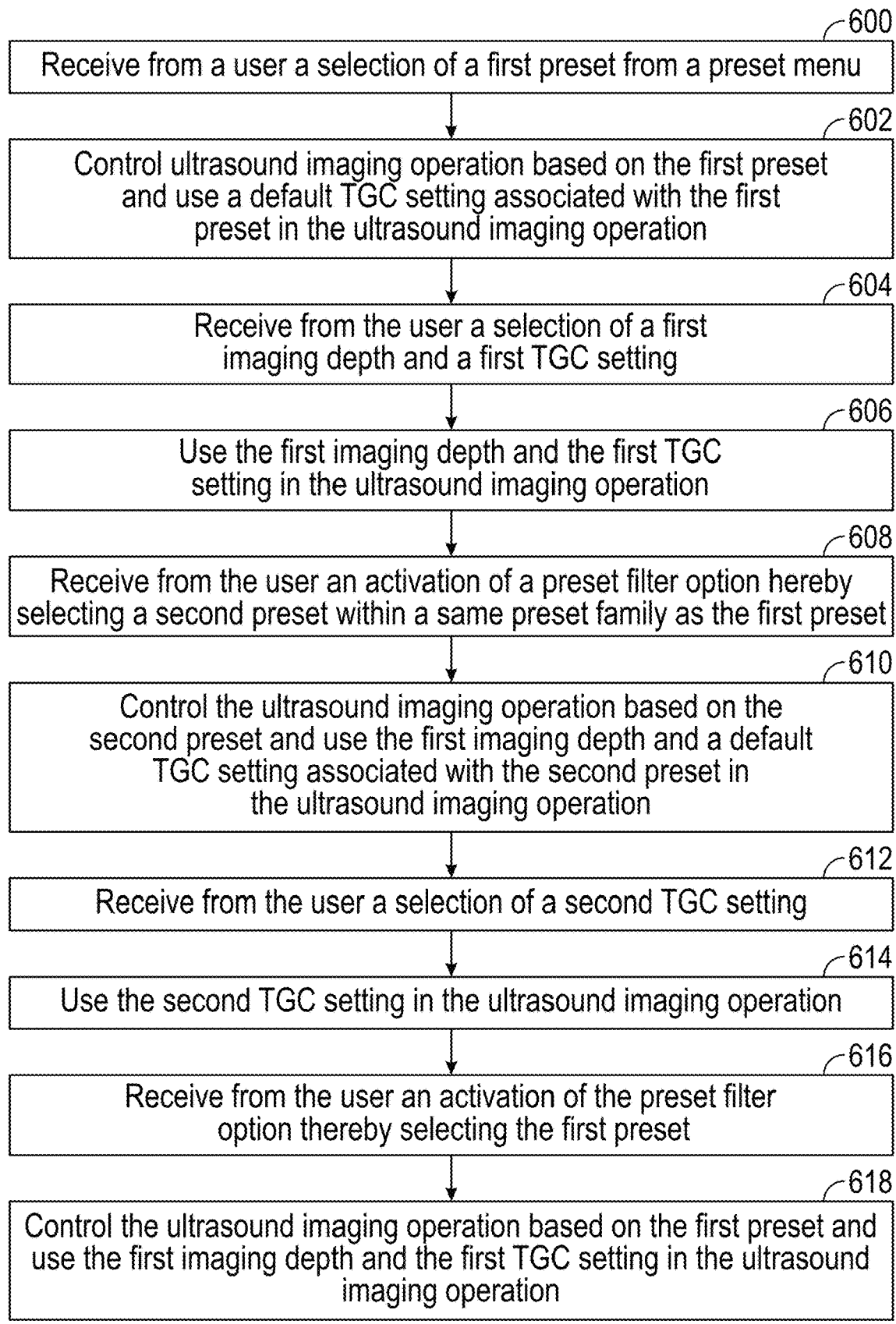

The method by which both imaging depth and TGC are used by the processing device 104 when presets are selected by a user using the GUI 200, and particularly the preset filter option 204, is shown in FIG. 20. The method of FIG. 20 may be an embodiment of the method of FIG. 17 with the addition of certain features. The method of FIG. 20 is a combination of the methods of FIG. 18 and FIG. 19.

At step 600, the processing device 104 receives from a user a selection of a first preset from the preset menu 152 displayed by the processing device 104. At step 602, the processing device 104 controls ultrasound imaging operation based on a first preset and uses a default TGC setting associated with the first preset in ultrasound imaging operation and a default imaging depth. Step 602 may be the same as step 502 or 302, with the additional feature that a default imaging depth associated with the first preset is used.

At step 604, the processing device 104 receives from the user a selection of a first TGC setting and imaging depth, and at step 606, the processing device 104 uses the first TGC setting and the imaging depth in the ultrasound imaging operation. At step 608, the processing device 104 receives from the user an activation of the preset filter option 204 thereby selecting a second preset within a same preset family as the first preset.

At step 610, the processing device 104 controls the ultrasound imaging operation based on the second preset and uses a default TGC setting associated with the second preset in the ultrasound imaging operation while still using the first (i.e., default) imaging depth. Further description of using a TGC setting may be found with reference to step 602.

At step 612, the processing device 104 receives from the user a selection of a second TGC setting, and at step 614, the processing device 104 uses the second TGC setting in the ultrasound imaging operation. At step 616, the processing device 104 receives from the user an activation of the preset filter option 204 thereby selecting the first preset. At step 618, the processing device 104 controls the ultrasound imaging operation based on the first preset and uses the first TGC setting and the default imaging depth in the ultrasound imaging operation. Thus, the imaging depth is retained while cycling between different presets within a preset family unless changed by the user. Additionally, TGC settings may not be retained when cycling from one preset to another within a preset family. Rather, the most recently used TGC setting for a particular preset may be used.

In some embodiments, a gain setting may operate in a similar manner as described above for TGC. TGC and gain may not persist when a preset is switched using the preset filter option 204 because gain and TGC may both vary the ultrasound images and may be preset dependent-parameters, while the imaging depth may be an anatomy-dependent parameter so the anatomy at issue should remain at the same depth regardless of the preset.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

It will be appreciated that of the above-disclosed and other features and functions, or alternatives thereof, may be desirably combined into many other different systems or applications. Various presently unforeseen or unanticipated alternatives, modifications, variations or improvements may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A smartphone or tablet in operative communication with an ultrasound device, the smartphone or tablet comprising:
 a processor configured to:
  receive from a user a selection of a first preset from a preset menu displayed by the smartphone or tablet, wherein the preset menu comprises a plurality of user-selectable presets;
  control ultrasound imaging operation based on the first preset, wherein controlling the ultrasound imaging operation comprises controlling ultrasound imaging operation of the ultrasound device and ultrasound imaging operation of the smartphone or tablet, and use a default imaging depth associated with the first preset and a default time-gain compensation (TGC) setting associated with the first preset in the ultrasound imaging operation;
  receive from the user a selection of a first imaging depth different from the default imaging depth and a first TGC setting different from the default TGC setting associated with the first preset;
  use the first imaging depth and the first TGC setting in the ultrasound imaging operation;
  receive from the user an activation of a preset filter option displayed by the smartphone or tablet, thereby selecting a second preset within a same preset family as the first preset;
  control the ultrasound imaging operation based on the second preset and use the first imaging depth and a default TGC setting associated with the second preset and different from the first TGC setting in the ultrasound imaging operation;
receive from the user a selection of second TGC setting different from the default TGC setting associated with the second preset and different from the first TGC setting;
use the first imaging depth and the second TGC setting in the ultrasound imaging operation;
receive from the user an activation of the preset filter option, thereby selecting the first preset; and
control the ultrasound imaging operation based on the first preset and use the first imaging depth and the first TGC setting in the ultrasound imaging operation.

2. The smartphone or tablet according to claim 1, wherein the first preset and the second preset each include a different set of ultrasound imaging parameter values that control transmit, analog processing, digital pre-processing and beamforming, coherent post-processing, and incoherent post-processing.

3. The smartphone or tablet according to claim 1, wherein the preset family comprises a plurality of presets optimized for imaging a same anatomy, a same anatomical region, and/or a same type of anatomy.

4. The smartphone or tablet according to claim 1, wherein the first preset comprises a standard preset and the second preset comprises a deep preset.

5. The smartphone or tablet according to claim 1, wherein the first preset comprises a harmonics preset and the second preset comprises a fundamentals preset.

6. The smartphone or tablet according to claim 1, wherein the preset family comprises two or more of an abdomen preset, an abdomen deep preset, and an aorta and gallbladder preset.

7. The smartphone or tablet according to claim 1, wherein the preset family comprises two or more of a musculoskeletal (MSK) preset, an MSK soft tissue preset, and a small organ preset.

8. The smartphone or tablet according to claim 1, wherein the preset family comprises two or more of an obstetric first month and gynecological preset, and an obstetric second and third months preset.

9. The smartphone or tablet according to claim 1, wherein the first preset comprises a vascular access preset and the second preset comprises a carotid preset.

10. The smartphone or tablet according to claim 1, wherein the preset family comprises two or more of a lung artifacts preset, a lung consolidation preset, and a lung tissue preset.

11. The smartphone or tablet according to claim 1, wherein repeated activation of the preset filter option cycles through presets within the preset family.

12. The smartphone or tablet according to claim 1, wherein a number of presets in the preset family is smaller than a number of the plurality of user-selectable presets in the preset menu.

13. The smartphone or tablet according to claim 1, wherein a subset of the plurality of user-selectable presets in the preset menu are not in preset families.

14. The smartphone or tablet according to claim 13, wherein the smartphone or tablet is configured to not display the preset filter option if a user selects a preset in the subset.

15. The smartphone or tablet according to claim 1, wherein the smartphone or tablet is configured to not display a subset of available presets in the preset menu.

16. The smartphone or tablet according to claim 1, wherein the smartphone or tablet is configured to display the first preset and the second preset in the preset menu.

17. The smartphone or tablet according to claim 1, wherein the ultrasound device comprises an ultrasound-on-chip.

18. The smartphone or tablet according to claim 1, wherein the processor is configured, when controlling the ultrasound imaging operation of the ultrasound device, to transmit commands to the ultrasound device to configure the ultrasound device with parameter values of the first preset.

19. The smartphone or tablet according to claim 1, wherein the processor is configured to save the first TGC setting prior to or upon receiving from the user the activation of the preset filter thereby selecting the second preset.

* * * * *